US006541008B1

(12) United States Patent
Wise et al.

(10) Patent No.: US 6,541,008 B1
(45) Date of Patent: Apr. 1, 2003

(54) VASCULAR ENDOTHELIAL GROWTH FACTOR-LIKE PROTEIN FROM ORF VIRUSES BINDS AND ACTIVATES MAMMALIAN VEGF RECEPTOR-2, AND USES THEREOF

(75) Inventors: Lyn M. Wise, Dunedin (NZ); Andrew A. Mercer, Dunedin (NZ); Loreen J. Savory, Dunedin (NZ); Stephen B. Fleming, Dunedin (NZ); Steven A. Stacker, Parkville (AU)

(73) Assignees: University of Otago, Dunedin (NZ); Ludwig Institute for Cancer Research, New York, NY (US)

( * ) Notice: Subject to any disclaimer, the term of this patent is extended or adjusted under 35 U.S.C. 154(b) by 0 days.

(21) Appl. No.: 09/431,888

(22) Filed: Nov. 2, 1999

Related U.S. Application Data

(60) Provisional application No. 60/106,689, filed on Nov. 2, 1998, and provisional application No. 60/106,800, filed on Nov. 3, 1998.

(51) Int. Cl.$^7$ .................. A61K 39/00; A61K 38/00; C07K 17/00
(52) U.S. Cl. .................. 424/198.1; 530/350; 514/2
(58) Field of Search .................. 514/2; 530/350; 424/198.1

(56) References Cited

PUBLICATIONS

Thomas, J. Biol. Chem. vol. 271, pp. 603–606, 1996.*
Proudfoot et al., J. Biol. Chem. vol. 271, pp. 2599–2603, 1996.*
Ogawa et al., JBC—A New Type of Endothelial Growth Factor VEGF–E, vol. 1273, pp. 31273–31282, 1998.
Wise et al., P.N.A.S.—Vascular Endothelial Growth Factor (VEGF)–Like Protein From ORF Virus NZ2 Binds to VEGFR2 and Neuropilin–1, vol. 96, pp. 3071–3076, 1999.
Meyer et al.—A Novel Vascular Endothelial Growth Factor Encoded by ORF Virus, VEGF–E, Mediates Angiogensis via Signalling through VEGFR–2 (KDR) but not VEGFR–1 (Flt–1) receptor Tyrosine Kinases, vol. 18, pp. 363–374, 1999.
Lyttle et al, Journal of Virology, Homologs of Vascular Endothelial Growth Factor Are Encoded by the Poxvirus ORF Virus, vol. 68, pp. 84–92, 1994.
Napoleone Ferrara, et al., "The Biology of Vascular Endothelial Growth Factor" Endocrine Reviews, vol. 18, No. 1, 1997.
Emmanuel Fournier, et al., "Receptors for factors of the VEGF family" Bull Cancer, 1997, vol. 84, pp. 397–403.
David M. Haig, et al., "Orf" Vet Research, vol. 29, pp. 311–326, 1998.
Copy of Supplemental European Search Report.

* cited by examiner

*Primary Examiner*—Yvonne Eyler
*Assistant Examiner*—Janet L. Andres
(74) *Attorney, Agent, or Firm*—Crowell & Moring LLP

(57) ABSTRACT

The invention is based on the discovery that a viral VEGF-like protein from the orf virus strain NZ2 and from the orf virus strain NZ10 is capable of binding to the extracellular domain of the VEGF receptor-2 to form bioactive complexes which mediate useful cellular responses and/or antagonize undesired biological activities. Disclosed are methods which stimulate or inhibit these biological activities, methods for therapeutic applications and antagonists of ORFV2-VEGF and/or NZ10.

17 Claims, 10 Drawing Sheets

ATGAAGTTGCTCTGCGGCATACTAGTAGCCGTGTGCTTGCACCAGTATCTGCTGAACGCGGACAG
CAACACGAAAGGATGGTCCGAAGTGCTGAAAGGCAGCGAGTGCAAGCCTAGGCCGATTGTTGTTC
CTGTAAGCGGAGACGCACCCAGAGCTGACTTCTCAGCGGTTCAACCCGTGTCACGTTGATG
CGATGCGGGCGGGGTGCTGCAACGACGAGAGCTTGGAATGCGTCCCACGAAGAAGTAAACGTGAC
GATGGAACTCCTGGGGCGTCGGGCTCCGTAGTAACGGATCAACGTCTGAGCTTCGTAGAGC
ATAAGAAATGCGATTGTAGACCACGATTCACAACCACCGCCCACCGACGACCACAAGGCCCGCCAGA
AGACGCCGCTAG

FIG. 8

MKLLVGILVAVCLHQYLLNADSNTKGWSEVLKGSECKPRPIVVPVSETHPELTSQRFNPPCVTLM
RCGGCCNDESLECVPTEEVNVTMELLGASGSGSNGMQRLSFVEHKKCDCRPRFTTPPTTTRPPR
RRR

```
atgaagttgc tcgtcggcat actggtagcc gtgtgcttgc accagtatct gctgaacgcg  60
gacagcacga aaacatggtc cgaggtgttt gaaagcagta agtgcaagcc aaggccaacg 120
gtcgttcccg taggcgaggc gcacccagag ctaacttctc agcggttcaa cccgcagtgt 180
gtcacagtga tgcgatgcgg cgggtgctgc aacgacgaga gcttggaatg cgtccccacg 240
gaagaggcaa acgtgacgat gcaactcatg ggggcgtcgg tctccggtgg taacgggatg 300
caacatttga tattcgtaga gcataagaaa tgcgattgta aaccacgact cacaaccacg 360
ccaccgacga ccacaaggcc gcccagaaga cgccgctag                        399
```

Fig. 11

Met Lys Leu Leu Val Gly Ile Leu Val Ala Val Cys Leu His Gln Tyr
 1               5                  10                  15

Leu Leu Asn Ala Asp Ser Thr Lys Thr Trp Ser Glu Val Phe Glu Ser
                20                  25                  30

Ser Lys Cys Lys Pro Arg Pro Thr Val Val Pro Val Gly Glu Ala His
                35                  40                  45

Pro Glu Leu Thr Ser Gln Arg Phe Asn Pro Gln Cys Val Thr Val Met
        50                  55                  60

Arg Cys Gly Gly Cys Cys Asn Asp Glu Ser Leu Glu Cys Val Pro Thr
65                  70                  75                  80

Glu Glu Ala Asn Val Thr Met Gln Leu Met Gly Ala Ser Val Ser Gly
                85                  90                  95

Gly Asn Gly Met Gln His Leu Ile Phe Val Glu His Lys Lys Cys Asp
                100                 105                 110

Cys Lys Pro Arg Leu Thr Thr Thr Pro Pro Thr Thr Thr Arg Pro Pro
        115                 120                 125

Arg Arg Arg Arg
130

VASCULAR ENDOTHELIAL GROWTH FACTOR-LIKE PROTEIN FROM ORF VIRUSES BINDS AND ACTIVATES MAMMALIAN VEGF RECEPTOR-2, AND USES THEREOF

CROSS REFERENCE TO RELATED APPLICATIONS

This application claims the benefit of U.S. Provisional Application No. 60/106,689, filed Nov. 2, 1998; and U.S. Provisional Application No. 60/106,800, filed Nov. 3, 1998.

FIELD OF THE INVENTION

This invention relates to viral vascular endothelial growth factor-like proteins which binds and activates the mammalian VEGF receptor-2 to induce vascular permeability of endothelial cells, and in particular to pharmaceutical and diagnostic compositions and methods utilizing or derived from the factor.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., Enzyme & Protein, 1996 49 138–162; Breier et al., Dev. Dyn. 1995 204 228–239; Risau, Nature, 1997 386 671–674). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Inhibition of angiogenesis is useful in preventing or alleviating these pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation. The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGF$\alpha$), and hepatocyte growth factor (HGF). See for example Folkman et al., J. Biol. Chem., 1992 267 10931–10934 for a review.

It has been suggested that a particular family of endothelial cell-specific growth factors, the vascular endothelial growth factors (VEGFs), and their corresponding receptors is primarily responsible for stimulation of endothelial cell growth and differentiation, and for certain functions of the differentiated cells. These factors are members of the PDGF family, and appear to act primarily via endothelial receptor tyrosine kinases (RTKs).

Nine different proteins have been identified in the PDGF family, namely two PDGFs (A and B), VEGF and six members that are closely related to VEGF. The six members closely related to VEGF are: VEGF-B, described in International Patent Application PCT/US96/02957 (WO 96/26736) and in U.S. Pat. Nos. 5,840,693 and 5,607,918 by Ludwig Institute for Cancer Research and The University of Helsinki; VEGF-C, described in Joukov et al., EMBO J., 1996 15 290–298 and Lee et al., Proc. Natl. Acad. Sci. USA, 1996 93 1988–1992; VEGF-D, described in International Patent Application No. PCT/US97/14696 (WO 98/07832), and Achen et al., Proc. Natl. Acad. Sci. USA, 1998 95 548–553; the placenta growth factor (PlGF), described in Maglione et al., Proc. Natl. Acad. Sci. USA, 1991 88 9267–9271; VEGF2, described in International Patent Application No. PCT/US94/05291 (WO 95/24473) by Human Genome Sciences, Inc; and VEGF3, described in International Patent Application No. PCT/US95/07283 (WO 96/39421) by Human Genome Sciences, Inc. Each VEGF family member has between 30% and 45% amino acid sequence identity with VEGF. The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Vascular endothelial growth factor (VEGF) is a homodimeric glycoprotein that has been isolated from several sources. VEGF shows highly specific mitogenic activity for endothelial cells. VEGF has important regulatory functions in the formation of new blood vessels during embryonic vasculogenesis and in angiogenesis during adult life (Carmeliet et al., Nature, 1996 380 435–439; Ferrara et al., Nature, 1996 380 439–442; reviewed in Ferrara and Davis-Smyth, Endocrine Rev., 1997 18 4–25). The significance of the role played by VEGF has been demonstrated in studies showing that inactivation of a single VEGF allele results in embryonic lethality due to failed development of the vasculature (Carmeliet et al., Nature, 1996 380 435–439; Ferrara et al., Nature, 1996 380 439–442). In addition VEGF has strong chemoattractant activity towards monocytes, can induce the plasminogen activator and the plasminogen activator inhibitor in endothelial cells, and can also induce microvascular permeability. Because of the latter activity, it is sometimes referred to as vascular permeability factor (VPF). The isolation and properties of VEGF have been reviewed; see Ferrara et al., J. Cellular Biochem., 1991 47 211–218 and Connolly, J. Cellular Biochem., 1991 47 219–223. Alterative mRNA splicing of a single VEGF gene gives rise to five isoforms of VEGF.

VEGF-B has similar angiogenic and other properties to those of VEGF, but is distributed and expressed in tissues differently from VEGF. In particular, VEGF-B is very strongly expressed in heart, and only weakly in lung, whereas the reverse is the case for VEGF. This suggests that VEGF and VEGF-B, despite the fact that they are co-expressed in many tissues, may have functional differences.

VEGF-B was isolated using a yeast co-hybrid interaction trap screening technique by screening for cellular proteins which might interact with cellular resinoid acid-binding protein type I (CRABP-I). Its isolation and characteristics are described in detail in PCT/US96/02957 and in olofsson et al., Proc. Natl. Acad. Sci. USA, 1996 93 2576–2581.

VEGF-C was isolated from conditioned media of the PC-3 prostate adenocarcinoma cell line (CRL1435) by screening for ability of the medium to produce tyrosine phosphorylation of the endothelial cell-specific receptor tyrosine kinase VEGFR-3 (Flt4), using cells transfected to express VEGFR-3. VEGF-C was purified using affinity chromatography with recombinant VEGFR-3, and was cloned from a PC-3 cDNA library. Its isolation and characteristics are described in detail in Joukov et al., EMBO J., 1996 15 290–298.

VEGF-D was isolated from a human breast cDNA library, commercially available from Clontech, by screening with an expressed sequence tag obtained from a human cDNA library designated "Soares Breast 3NbHBst" as a hybridization probe (Achen et al., Proc. Natl. Acad. Sci. USA, 1998 95 548–553). Its isolation and characteristics are described in detail in International Patent Application No. PCT/US97/14696 (WO98/07832)

The VEGF-D gene is broadly expressed in the adult human, but is certainly not ubiquitously expressed. VEGF-D is strongly expressed in heart, lung and skeletal muscle. Intermediate levels of VEGF-D are expressed in spleen, ovary, small intestine and colon, and a lower expression occurs in kidney, pancreas, thymus, prostate and testis. No VEGF-D mRNA was detected in RNA from brain, placenta, liver or peripheral blood leukocytes.

PlGF was isolated from a term placenta cDNA library. Its isolation and characteristics are described in detail in Maglione et al., Proc. Natl. Acad. Sci. USA, 1991 88 9267–9271. Presently its biological function is not well understood.

VEGF2 was isolated from a highly tumorgenic, oestrogen-independent human breast cancer cell line. While this molecule is stated to have about 22% homology to PDGF and 30% homology to VEGF, the method of isolation of the gene encoding VEGF2 is unclear, and no characterization of the biological activity is disclosed.

VEGF3 was isolated from a cDNA library derived from colon tissue. VEGF3 is stated to have about 36% identity and 66% similarity to VEGF. The method of isolation of the gene encoding VEGF3 is unclear and no characterization of the biological activity is disclosed.

Similarity between two proteins is determined by comparing the amino acid sequence and conserved amino acid substitutions of one of the proteins to the sequence of the second protein, whereas identity is determined without including the conserved amino acid substitutions.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., The EMBO Journal, 1996 15 290–298). VEGF-D binds to both VEGFR-2 and VEGFR-3. A ligand for Tek/Tie-2 has been described in International Patent Application No. PCT/US95/12935 (WO 96/11269) by Regeneron Pharmaceuticals, Inc. The ligand for Tie has not yet been identified.

Recently, a novel 130–135 kDa VEGF isoform specific receptor has been purified and cloned (Soker et al., Cell, 1998 92 735–745). The VEGF receptor was found to specifically bind the $VEGF_{165}$ isoform via the exon 7 encoded sequence, which shows weak affinity for heparin (Soker et al., Cell, 1998 92 735–745). Surprisingly, the receptor was shown to be identical to human neuropilin-1 (NP-1), a receptor involved in early stage neuromorphogenesis. PlGF-2 also appears to interact with NP-1 (Migdal et al., J. Biol. Chem., 1998 273 22272–22278).

VEGFR-1, VEGFR-2 and VEGFR-3 are expressed differently by endothelial cells. Both VEGFR-1 and VEGFR-2 are expressed in blood vessel endothelia (Oelrichs et al., Oncogene, 1992 8 11–18; Kaipainen et al., J. Exp. Med., 1993 178 2077–2088; Dumont et al., Dev. Dyn., 1995 203 80–92; Fong et al., Dev. Dyn., 1996 207 1–10) and VEGFR-3 is mostly expressed in the lymphatic endothelium of adult tissues (Kaipainen et al., Proc. Natl. Acad. Sci. USA, 1995 9 3566–3570). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., Nature, 1995 376 66–70). However, deletion of the intracellular tyrosine kinase domain of VEGFR-1 generates viable mice with a normal vasculature (Hiratsuka et al., Proc. Natl. Acad. Sci. USA 1998 95 9349–9354). The reasons underlying these differences remain to be explained but suggest that receptor signalling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., Nature, 1995 376 62–66; Shalaby et al., Cell, 1997 89 981–990). Inactivation of VEGFR-3 results in cardiovascular failure due to abnormal organization of the large vessels (Dumont et al. Science, 1998 282 946–949).

Although VEGFR-1 is mainly expressed in endothelial cells during development, it can also be found in hematopoetic precursor cells during early stages of embryogenesis (Fong et al., Nature, 1995 376 66–70). In adults, monocytes and macrophages also express this receptor (Barleon et al., Blood, 1996 87 3336–3343). In embryos, VEGFR-1 is expressed by most, if not all, vessels (Breier et al., Dev. Dyn., 1995 204 228–239; Fong et al., Dev. Dyn., 1996 207 1–10).

The receptor VEGFR-3 is widely expressed on endothelial cells during early embryonic development but as embryogenesis proceeds becomes restricted to venous endothelium and then to the lymphatic endothelium (Kaipainen et al., Cancer Res., 1994 54 6571–6577; Kaipainen et al., Proc. Natl. Acad. Sci. USA, 1995 92 3566–3570). VEGFR-3 is expressed on lymphatic endothelial cells in adult tissues. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., EMBO J., 1996 15 290–298).

Some inhibitors of the VEGF/VEGF-receptor system have been shown to prevent tumor growth via an antiangiogenic mechanism; see Kim et al., Nature, 1993 362 841–844 and Saleh et al., Cancer Res., 1996 56 393–401.

In addition, VEGF-like proteins have been identified which are encoded by four different strains of the orf virus. This is the first virus reported to encode a VEGF-like protein. The first two strains are NZ2 and NZ7, and are described in Lyttle et al., J. Virol., 1994 68 84–92. A third is D1701 and is described in Meyer et al., The EMBO Journal, 1999 18 363–374. The fourth strain is NZ10 and is described herein. These proteins show amino acid sequence similarity to VEGF and to each other.

The orf virus is a type of species of the parapoxvirus genus which causes a highly contagious pustular dermatitis in sheep and goats and is readily transmittable to humans. The pustular dermatitis induced by orf virus infection is characterized by dilation of blood vessels, swelling of the local area and marked proliferation of endothelial cells lining the blood vessels. These features are seen in all species infected by orf and can result in the formation of a tumor-like growth or nodule due to viral replication in epidermal cells. Generally orf virus infections resolve in a few weeks but severe infections that fail to resolve without surgical intervention are seen in immune impaired individuals. The finding that the orf virus strains NZ2 and NZ7 encode molecules with VEGF-like sequences raises the important question of whether these proteins are capable of binding to mammalian VEGF receptors and inducing characteristic VEGF-like effects such as mitogenesis of endothelial cells and vascular permeability.

SUMMARY OF THE INVENTION

The invention is based on the discovery that a viral VEGF-like protein from the orf virus strains NZ2 (herein after referred to as ORFV2-VEGF or NZ2)and NZ10 are capable of binding to the extracellular domain of the VEGF receptor-2 to form bioactive complexes which mediate useful cellular responses and/or antagonize undesired biological activities. In addition, ORFV2-VEGF is capable of binding NP-1. The invention generally provides for methods which stimulate or inhibit these biological activities, methods for therapeutic applications and finding antagonists of ORFV2-VEGF or NZ10.

According to a first aspect, the invention provides an isolated and purified nucleic acid molecule which comprises a polynucleotide sequence having at least 85% identity, more preferably at least 90%, and most preferably at least 95% identity to at least the sequence set out in FIG. 10 (SEQ ID NO:10) and that encodes a novel polypeptide, designated ORFV10-VEGF (hereinafter NZ10), which is structurally homologous to VEGF and NZ2. This aspect of the invention also encompasses DNA molecules having a sequence such that they hybridize under stringent conditions with at least nucleotides of the sequence set out in FIG. 10 (SEQ ID NO:10) or fragments thereof.

According to a second aspect, the polypeptide of the invention has the ability to stimulate proliferation of endothelial cells and comprises a sequence of amino acids substantially corresponding to the amino acid sequence set out in FIG. 11 (SEQ ID NO:11), or a fragment or analog thereof which has the ability to stimulate one or more of endothelial cell proliferation, differentiation, migration or survival. Preferably the polypeptides have at least 85% identity, more preferably at least 90%, and most preferably at least 95% identity to the amino acid sequence of FIG. 11 (SEQ ID NO:11), or a fragment or analog thereof having the biological activity of NZ10.

According to another aspect, the invention provides for a method for stimulating one or more of endothelial cell proliferation, differentiation, migration or survival by exposing them to ORFV2-VEGF or NZ10 or a fragment or analog thereof which has the ability.

According to a further aspect, the invention provides a method for activation of VEGF receptor-2 which comprises the step of exposing cells bearing said receptor to an effective receptor activating dose of ORFV2-VEGF or NZ10 or a fragment or analog thereof which has the ability.

Since both ORFV2-VEGF and NZ10 specifically activate the VEGF receptor-2, ORFV2-VEGF can be used to stimulate endothelial cell proliferation in a situation where VEGF receptor 1 is not activated. Accordingly, the invention provides for a method for specific activation of VEGF receptor 2 and VEGF receptor 1 is not activated.

These abilities are referred to herein as "biological activities of ORFV2-VEGF or NZ10" and can readily be tested by methods known in the art, such as the mitogenic assay described in Example 5. In particular, ORFV2-VEGF and NZ10 have the ability to stimulate endothelial cell proliferation or differentiation, including, but not limited to, proliferation or differentiation of vascular endothelial cells and/or lymphatic endothelial cells.

More preferably ORFV2-VEGF has the amino acid sequence set out in FIG. 9 (SEQ ID NO:2), while NZ10 has the amino acid sequence set out in FIG. 10 (SEQ ID NO:11).

In another preferred aspect, the invention provides a polypeptides possessing the characteristic amino acid sequence:

Pro-Xaa-Cys-Xaa-Xaa-Xaa-Xaa-Arg-Cys-Xaa-Gly-Cys-Cys (SEQ ID NOs:9 and 11), which is characteristic of members of the PDGF/VEGF family of growth factors.

Polypeptides comprising conservative substitutions, insertions, or deletions, but which still retain the biological activity of ORFV2-VEGF or NZ10, are clearly to be understood to be within the scope of the invention. Persons skilled in the art will be well aware of methods which can readily be used to generate such polypeptides, for example the use of site-directed mutagenesis, or specific enzymatic cleavage and ligation. The skilled person will also be aware that peptidomimetic compounds or compounds in which one or more amino acid residues are replaced by a non-naturally occurring amino acid or an amino acid analogue may retain the required aspects of the biological activity of ORFV2-VEGF. Such compounds can readily be made and tested by methods known in the art, and are also within the scope of the invention.

In addition, variant forms of the ORFV2-VEGF or NZ10 polypeptide which result naturally-occurring allelic variants of the nucleic acid sequence encoding ORFV2-VEGF or ORFV10-VEGF are encompassed within the scope of the invention. Allelic variants are well known in the art, and represent alternative forms or a nucleic acid sequence which comprise substitution, deletion or addition of one or more nucleotides, but which do not result in any substantial functional alteration of the encoded polypeptide.

As used herein, the term "ORFV2-VEGF" collectively refers to the polypeptide having the amino acid sequence set forth in FIG. 9 (SEQ ID NO:2) and fragments or analogues thereof and other variants, for example, from natural isolates of the orf virus which have the biological activity of ORFV2-VEGF as herein defined. Those skilled in the art will recognize that there is considerable latitude in amino acid sequence charges which can occur naturally or be engineered without affecting biological activity of the polypeptide. It is preferred that the variant polypeptides be at least 80%, more preferably be at least 90%, and most preferably at least 95% identical to the amino acid sequence of FIG. 9 (SEQ ID NO:2). Percent sequence identity is determined by conventional methods. See, for example, Altschul et al, Bull. Math. Bio., 1986 48 603–616 and Henikoff and Henikoff, Proc. Natl. Acad. Sci. USA, 1992 89 10915–10919.

As used herein, the term "NZ10" collectively refers to the polypeptide having the amino acid sequence set forth in FIG. 11 (SEQ ID NO:11) and fragments or analogs thereof and other variants, for example, from natural isolates of the orf virus which have the biological activity of NZ10 as herein defined. Those skilled in the art will recognize that there is considerable latitude in amino acid sequence charges which can occur naturally or be engineered without affecting biological activity of the polypeptide. It is preferred that the variant polypeptides be at least 80%, more preferably be at least 90%, and most preferably at least 95% identical to the amino acid sequence of FIG. 11 (SEQ ID NO:11). Percent sequence identity is determined by conventional methods. See, for example, Altschul et al, Bull. Math. Bio., 1986 48 603–616 and Henikoff and Henikoff, Proc. Natl. Acad. Sci. USA, 1992 89 10915–10919.

Such variant forms of ORFV2-VEGF or NZ10 can be prepared by targeting non-essential regions of the ORFV2-VEGF or NZ10 polypeptide for modification. Other variant forms may be naturally made from related orf virus strains. These non-essential regions are expected to fall outside the strongly-conserved regions indicated in FIGS. 1A and 1B. In particular, the growth factors of the PDGF family, including VEGF, are dimeric, and VEGF, VEGF-B, VEGF-C, VEGF-D, ORFV2-VEGF, PlGF, PDGF-A and PDGF-B show complete conservation of eight cysteine residues in the N-terminal domains, ie. the PDGF-like domains (Olofsson et al, 1996; Joukov et al, 1996). These cysteines are thought to be involved in intra- and inter-molecular disulfide bonding. In addition there are further strongly, but not completely, conserved cysteine residues in the C-terminal domains. Loops 1, 2 and 3 of each subunit, which are formed by intra-molecular disulfide bonding, are involved in binding to the receptors for the PDGF/VEGF family of growth factors (Andersson et al: Growth Factors, 1995 12 159–164). As noted above, the cysteines conserved in previously known members of the VEGF family are also conserved in ORFV2-VEGF.

Persons skilled in the art thus are well aware that these cysteine residues should be preserved in any proposed variant form, and that the active sites present in loops 1, 2 and 3 also should be preserved. However, other regions of the molecule can be expected to be of lesser importance for biological function, and therefore offer suitable targets for modification. Modified polypeptides can readily be tested for their ability to show the biological activity of ORFV2-VEGF by routine activity assay procedures such as cell proliferation tests.

It is contemplated that some modified ORFV2-VEGF or NZ10 polypeptides will have the ability to bind to endothelial cells, e.g. to VEGF receptor-2, but will be unable to stimulate endothelial cell proliferation, differentiation, migration or survival. These modified polypeptides are expected to be able to act as competitive or non-competitive inhibitors of the ORFV2-VEGF or NZ10 polypeptides and growth factors of the PDGF/VEGF family, and to be useful in situations where prevention or reduction of the ORFV2-VEGF or NZ10 polypeptide or PDGF/VEGF family growth factor action is desirable. Thus such receptor-binding but non-mitogenic, non-differentiation inducing, non-migration inducing, non-motility inducing, non-survival promoting, non-connective tissue development promoting, non-wound healing or non-vascular proliferation inducing variants of the ORFV2-VEGF or NZ10 polypeptide are also within the scope of the invention, and are referred to herein as "receptor-binding but otherwise inactive variant". Because ORFV2-VEGF or NZ10 forms a dimer in order to activate its only known receptor, it is contemplated that one monomer comprises the receptor-binding but otherwise inactive variant modified ORFV2-VEGF or NZ10 polypeptide and a second monomer comprises a wild-type ORFV2-VEGF or NZ10 or a wild-type growth factor of the PDGF/VEGF family. These dimers can bind to its corresponding receptor but cannot induce downstream signaling.

It is also contemplated that there are other modified ORFV2-VEGF or NZ10 polypeptides that can prevent binding of a wild-type ORFV2-VEGF or NZ10 or a wild-type growth factor of the PDGF/VEGF family to its corresponding receptor on endothelial cells. Thus these dimers will be unable to stimulate endothelial cell proliferation, differentiation, migration or survival. These modified polypeptides are expected to be able to act as competitive or non-competitive inhibitors of the ORFV2-VEGF or NZ10 polypeptide or a growth factor of the PDGF/VEGF family, and to be useful in situations where prevention or reduction of the ORFV2-VEGF or NZ10 polypeptide or PDGF/VEGF family growth factor action is desirable. Such situations include the tissue remodeling that takes place during invasion of tumor cells into a normal cell population by primary or metastatic tumor formation. Thus such the ORFV2-VEGF or NZ10 or PDGF/VEGF family growth factor-binding but non-mitogenic, non-differentiation inducing, non-migration inducing, non-motility inducing, non-survival promoting, non-connective tissue promoting, non-wound healing or non-vascular proliferation inducing variants of the ORFV2-VEGF or NZ10 polypeptide are also within the scope of the invention, and are referred to herein as "the ORFV2-VEGF or NZ10 polypeptide-dimer forming but otherwise inactive or interfering variants".

Thus, another aspect of the invention is a ORFV2-VEGF or NZ10 antagonist, wherein the antagonist is an isolated polypeptide which comprises a sequence of amino acids substantially corresponding to the amino acid sequence of FIG. 9 (SEQ ID NO:2) or FIG. 11 (SEQ ID NO:11), repsectively and has the ability to bind to ORFV2-VEGF or NZ10 and to prevent biological activity of ORFV2-VEGF or NZ10.

As noted above, the orf virus is known to cause a pustular dermatitis in sheep, goats and humans. The lesions induced after infection with orf virus show extensive proliferation of vascular endothelial cells, dilation of blood vessels and dermal swelling. Expression of an orf virus gene able to stimulate angiogenesis may provide an explanation for these histological observations.

Accordingly, a further aspect of the invention provides a method for treatment of pustular dermatitis and of fluid accumulation caused by viral infection which comprises the step of administering a therapeutically effective amount of an antagonist to ORFV2-VEGF or NZ10 or to the VEGF receptor 2.

Where ORFV2-VEGF, NZ10 or a ORFV2-VEGF antagonist or NZ10 antagonist is to be used for therapeutic purposes, the dose and route of application will depend upon the condition to be treated, and will be at the discretion of the attending physician or veterinarian. Suitable routes include subcutaneous, intramuscular, intraperitoneal or intravenous injection, topical application, implants etc. Topical application of ORFV2-VEGF or NZ10 may be used in a manner analogous to VEGF.

Another aspect of the invention provides expression vectors comprising the DNA of the invention or a nucleic acid molecule of the invention, and host cells transformed or transfected with nucleic acids molecules or vectors of the invention. Vectors also comprises a nucleic acid sequence which hybridize under stringent conditions with the sequence of FIG. 8 or FIG. 10. These cells are particularly suitable for expression of the polypeptide of the invention, and include insect cells such as Sf9 cells, obtainable from the American Type Culture Collection (ATCC SRL-171), transformed with a baculovirus vector, and the human embryo kidney cell line 293 EBNA transfected by a suitable expression plasmid. Preferred vectors of the invention are expression vectors in which a nucleic acid according to the invention is operatively connected to one or more appropriate promoters and/or other control sequences, such that appropriate host cells transformed or transfected with the vectors are capable of expressing the polypeptide of the invention. Other preferred vectors are those suitable for transfection of mammalian cells, or for gene therapy, such as adenoviral-, vaccinia- or retroviral-based vectors or liposomes. A variety of such vectors is known in the art.

The invention also provides a method of making a vector capable of expressing a polypeptide encoded by a nucleic acid according to the invention, comprising the steps of operatively connecting the nucleic acid to one or more appropriate promoters and/or other control sequences, as described above.

The invention further provides a method of making a polypeptide according to the invention, comprising the steps of expressing a nucleic acid or vector according to the invention in a host cell, and isolating the polypeptide from the host cell or from the host cell's growth medium.

In yet a further aspect, the invention provides an antibody specifically reactive with ORFV2-VEGF or NZ10. This aspect of the invention includes antibodies specific for the variant forms, fragments and analogues of ORFV2-VEGF or NZ10 referred to above. The term "analog" or "functional analog" refers to a modified form of ORFV2-VEGF or NZ10 in which at least one amino acid substitution has been made such that said analog retains substantially the same biological activity as the unmodified ORFV2-VEGF and/or NZ10 in vivo and or in vitro. Such antibodies are useful as inhibitors or agonists of ORFV2-VEGF or NZ10 and as diagnostic agents for detecting and quantifying ORFV2-VEGF and/or NZ10. Polyclonal or monoclonal antibodies may be used. Monoclonal and polyclonal antibodies can be raised against polypeptides of the invention using standard methods in the art. For some purposes, for example where a monoclonal antibody is to be used to inhibit effects of ORFV2-VEGF and/or NZ10 in a clinical situation, it may be desirable to use humanized or chimeric monoclonal antibodies. In addition the polypeptide can be linked to an epitope tag, such as the FLAG® octapeptide (Sigma, St. Louis, Mo.), to assist in affinity purification. For some purposes, for example where a monoclonal antibody is to be used to inhibit effects of PDGF-C in a clinical situation, it may be desirable to use humanized or chimeric monoclonal antibodies. Such antibodies may be further modified by addition of cytotoxic or cytostatic drugs. Methods for producing these, including recombinant DNA methods, are also well known in the art.

This aspect of the invention also includes an antibody which recognizes ORFV2-VEGF and which is suitably labeled.

Polypeptides or antibodies according to the invention may be labeled with a detectable label, and utilized for diagnostic purposes. Similarly, the thus-labeled polypeptide of the invention may be used to identify its corresponding receptor in situ. The polypeptide or antibody may be covalently or non-covalently coupled to a suitable supermagnetic, paramagnetic, electron dense, ecogenic or radioactive agent for imaging. For use in diagnostic assays, radioactive or non-radioactive labels may be used. Examples of radioactive labels include a radioactive atom or group, such as $^{125}$I or $^{32}$P. Examples of non-radioactive labels include enzymatic labels, such as horseradish peroxidase or fluorimetric labels, such as fluorescein-5-isothiocyanate (FITC). Labeling may be direct or indirect, covalent or non-covalent.

Clinical applications of the invention include diagnostic applications, acceleration of angiogenesis in wound healing, tissue or organ transplantation, or to establish collateral circulation in tissue infarction or arterial stenosis, such as coronary artery disease, and inhibition of angiogenesis in the treatment of cancer or of diabetic retinopathy.

Conversely, ORFV2-VEGF and/or NZ10 antagonists (e.g. antibodies and/or inhibitors) could be used to treat conditions, such as congestive heart failure, involving accumulations of fluid in, for example, the lung resulting from increases in vascular permeability, by exerting an offsetting effect on vascular permeability in order to counteract the fluid accumulation. Administrations of ORFV2-VEGF could be used to treat malabsorptive syndromes in the intestinal tract as a result of its blood circulation increasing and vascular permeability increasing activities.

Thus the invention provides a method of stimulation of angiogenesis and/or neovascularization in a mammal in need of such treatment, comprising the step of administering an effective dose of ORFV2-VEGF or NZ10, or a fragment or analog thereof which has the ability to stimulate endothelial cell proliferation, to the mammal.

Optionally ORFV2-VEGF may be administered together with, or in conjunction with, one or more of VEGF, VEGF-B, VEGF-C, VEGF-D, PlGF, PDGF, FGF and/or heparin.

Conversely the invention provides a method of inhibiting angiogenesis and/or neovascularization in a mammal in need of such treatment, comprising the step of administering an effective amount of an antagonist of ORFV2-VEGF to the mammal. The antagonist may be any agent that prevents the action of ORFV2-VEGF and/or NZ10, either by preventing the binding of ORFV2-VEGF and/or NZ10 to its corresponding receptor or the target cell, or by preventing activation of the transducer of the signal from the receptor to its cellular site of action. Suitable antagonists include, but are not limited to, antibodies directed against ORFV2-VEGF and/or NZ10; competitive or non-competitive inhibitors of binding of ORFV2-VEGF/NZ10 to the ORFV2-VEGF/NZ10 receptor, such as the receptor-binding but non-mitogenic ORFV2-VEGF or NZ10 variants referred to above; and anti-sense nucleotide sequences complementary to at least a part of the DNA sequence encoding ORFV2-VEGF and/or NZ10.

The invention also provides a method of detecting ORFV2-VEGF and/or NZ10 in a biological sample, comprising the step of contacting the sample with a reagent capable of binding ORFV2-VEGF, and detecting the binding. Preferably the reagent capable of binding ORFV2-VEGF and/or NZ10 is an antibody directed against ORFV2-VEGF and/or NZ10, particularly preferably a monoclonal antibody. In a preferred embodiment the binding and/or extent of binding is detected by means of a detectable label; suitable labels are discussed above.

According to yet a further aspect, the invention provides diagnostic means typically in the form of test kits. For example, in one embodiment of the invention there is provided a diagnostic test kit comprising an antibody to ORFV2-VEGF and/or NZ10 and means for detecting, and more preferably evaluating, binding between the antibody and ORFV2-VEGF or NZ10. In one preferred embodiment of the diagnostic means according to the invention, either the antibody or the ORFV2-VEGF or NZ10 is labelled with a detectable label, and either the antibody or the ORFV2-VEGF or NZ10 is substrate-bound, such that the ORFV2-VEGF/ or NZ10/antibody interaction can be established by determining the amount of label attached to the substrate following binding between the antibody and the ORFV2-VEGF and/or NZ10. In a particularly preferred embodiment of the invention, the diagnostic means may be provided as a conventional ELISA kit.

A method is provided for determining agents that bind to ORFV2-VEGF and/or NZ10. The method comprises contacting ORFV2-VEGF or NZ10 with a test agent and monitoring binding by any suitable means. Agents can include both compounds and other proteins.

The invention provides a screening system for discovering agents that bind ORFV2-VEGF and/or NZ10. The screening system comprises preparing ORFV2-VEGF or NZ10, exposing ORFV2-VEGF or NZ10 to a test agent, and quantifying the binding of said agent to ORFV2-VEGF or NZ10 by any suitable means.

Use of this screen system provides a means to determine compounds that may alter the biological function of ORFV2-VEGF or NZ10. This screening method may be adapted to large-scale, automated procedures such as a PANDEX® (Baxter-Dade Diagnostics) system, allowing for efficient high-volume screening of potential therapeutic agents.

For this screening system, ORFV2-VEGF or NZ10 is prepared as described herein, preferably using recombinant DNA technology. A test agent, e.g. a compound or protein, is introduced into a reaction vessel containing ORFV2-VEGF or NZ10. Binding of the test agent to ORFV2-VEGF or NZ10 is determined by any suitable means which include, but is not limited to, radioactively- or chemically-labeling the test agent. Binding of ORFV2-VEGF or NZ10 may also be carried out by a method disclosed in U.S. Pat. No. 5,585,277, which is incorporated by reference. In this method, binding of the test agent to ORFV2-VEGF or NZ10 is assessed by monitoring the ratio of folded protein to unfolded protein. Examples of this monitoring can include, but are not limited to, amenability to binding of the protein by a specific antibody against the folded state of the protein.

Those of skill in the art will recognize that $IC_{50}$ values are dependent on the selectivity of the agent tested. For example, an agent with an $IC_{50}$ which is less than 10 nM is generally considered an excellent candidate for drug therapy. However, an agent which has a lower affinity, but is selective for a particular target, may be an even better candidate. Those skilled in the art will recognize that any information regarding the binding potential, inhibitory activity or selectivity of a particular agent is useful toward the development of pharmaceutical products.

Where a ORFV2-VEGF or NZ10 or a ORFV2-VEGF antagonist or a NZ10 antagonist is to be used for therapeutic purposes, the dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. Topical application of ORFV2-VEGF or NZ10 may be used in a manner analogous to VEGF. For example, where used for wound healing or other use in which enhanced angiogenesis is advantageous, an effective amount of ORFV2-VEGF or NZ10 is administered to an organism in need thereof in a dose between about 0.1 and 1000 µg/kg body weight.

The ORFV2-VEGF or NZ10 or a ORFV2-VEGF antagonist or a NZ10 antagonist may be employed in combination with a suitable pharmaceutical carrier. The resulting compositions comprise a therapeutically effective amount of ORFV2-VEGF or NZ10 or a ORFV2-VEGF antagonist or a NZ10 antagonist, and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation to suit the mode of administration. Compositions which comprise ORFV2-VEGF or NZ10 may optionally further comprise one or more of PDGF-A, PDGF-B, VEGF, VEGF-B, VEGF-C, VEGF-D, PlGF and/or heparin. Compositions comprising ORFV2-VEGF or NZ10 will contain from about 0.1% to 90% by weight of the active compound(s), and most generally from about 10% to 30%.

For intramuscular preparations, a sterile formulation, preferably a suitable soluble salt form of ORFV2-VEGF or NZ10, such as hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

Another aspect of the invention concerns the provision of a pharmaceutical composition comprising either ORFV2-VEGF or NZ10 or a fragment or analog thereof which promotes proliferation of endothelial cells, or an antagonist such as antibody thereto. Compositions which comprise ORFV2-VEGF or NZ10 may optionally further comprise one or more of VEGF, VEGF-B, VEGF-C, VEGF-D and/or heparin.

In another aspect, the invention relates to a protein dimer comprising ORFV2-VEGF or NZ10, particularly a disulfide-linked dimer. The protein dimers of the invention include both homodimers of ORFV2-VEGF or NZ10 and heterodimers of ORFV2-VEGF or NZ10 and VEGF, VEGF-B, VEGF-C, VEGF-D, PlGF or PDGF, or heterodimers of ORFV2-VEGF and NZ10.

According to a yet further aspect of the invention there is provided a ORFV2-VEGF and/or NZ10 antagonist which can be an anti-sense nucleotide sequence which is complementary to at least a part of a DNA sequence which encodes ORFV2-VEGF, NZ10 or a fragment or analog thereof which may be used to inhibit, or at least mitigate, ORFV2-VEGF and/or NZ10 expression. In addition an anti-sense nucleotide sequence can be to the promoter region of the ORVF2-VEGF or ORFV10-VEGF gene or other non-coding region of the gene which may be used to inhibit, or at least mitigate, ORFV2-VEGF and/or NZ10 expression. The use of an antagonist of this type to inhibit ORFV2-VEGF expression is favored in instances where ORFV2-VEGF expression is associated with a disease, for example pustular dermatitis. Transformation of such cells with a vector containing an anti-sense nucleotide sequence would suppress or retard angiogenesis, and so would inhibit or retard growth of lesions.

A still further aspect the invention relates to an isolated ORFV2-VEGF or NZ10 and VEGFR-2 complex. Isolation and purification of complexes could be effected by conventional procedures such as immunoaffinity purification using monoclonal antibodies according to techniques described in standard reference work such as Harlow et al, "Antibodies, a Laboratory Manual", Cold Spring Harbor Laboratory Press, 1988 and/or Marshak et al, "Strategies for Protein Purification and Characterization", Cold Spring Harbor Laboratory Press, 1986.

Polynucleotides of the invention such as those described above, fragments of those polynucleotides, and variants of those polynucleotides with sufficient similarity to the non-coding strand of those polynucleotides to hybridize thereto under stringent conditions all are useful for identifying, purifying, and isolating polynucleotides encoding other, viral forms of VEGF-like polypeptides. Thus, such polynucleotide fragments and variants are intended as aspects of the invention. Exemplary stringent hybridization conditions are as follows: hybridization at 42° C. in 5×SSC, 20 mM $NaPO_4$, pH 6.8, 50% formamide; and washing at 42° C. in 0.2×SSC. Those skilled in the art understand that it is desirable to vary these conditions empirically based on the length and the GC nucleotide base content of the sequences to be hybridized, and that formulas for determining such variation exist. See for example Sambrook et al, "Molecular Cloning: A Laboratory Manual", Second Edition, pages 9.47–9.51, Cold Spring Harbor, N.Y.: Cold Spring Harbor Laboratory (1989).

It will be clearly understood that nucleic acids and polypeptides of the invention may be prepared by synthetic means or by recombinant means, or may be purified from natural sources.

It will be clearly understood that for the purposes of this specification the word "comprising" means "included but not limited to". The corresponding meaning applies to the word "comprises".

BRIEF DESCRIPTION OF THE DRAWINGS

FIGS. 1A and 1B show a comparative sequence alignment of the amino acid sequences of ORFV2-VEGF with other members of the VEGF family of growth factors. The deduced amino acid sequence of ORFV2-VEGF was aligned with the sequences of $VEGF_{121}$ (SEQ ID NO:3), $VEGF_{165}$ (SEQ ID NO:4), PlGF (SEQ ID NO:5), VEGF-$B_{167}$ (SEQ ID NO:6), and truncated sequences of VEGF-C (SEQ ID NO:7) and VEGF-D (SEQ ID NO:8). The residues which show identity with ORFV2-VEGF (SEQ ID NO:2) are boxed. The conserved cysteine residues of the cystine knot motif are indicated with an asterisk. The signal sequence as determined by N-terminal sequencing is indicated by the line above the sequence. The potential sites of N- and O-linked glycosylation are indicated by a bracket and dashed line respectively. The VEGF homology domain is indicated by arrows.

FIG. 2 shows the analysis and purification of expressed ORFV2-VEGF polypeptides.

(A) FLAG-tagged ORFV2-VEGF was expressed in COS cells by transient transfection. Cells were biosynthetically labeled with $^{35}$S-cysteine/methionine for 4 hours. Conditioned medium from these cells was immunoprecipitated with either M2-gel or control beads and the washed beads eluted with SDS-PAGE sample buffer under reducing (2% β-mercaptoethanol) or non-reducing conditions. The single arrow indicates the non-reduced form of ORFV2-VEGF and the double arrows the two species of the reduced form.

(B) Conditioned medium from COS cells transfected with FLAG-tagged ORFV2-VEGF DNA was purified on M2-gel and eluted with free FLAG peptide. The fractions (1: void; 2,3 and 4: purified protein) eluted from the M2-gel were collected, combined with 2×SDS-PAGE sample buffer (reducing), boiled and resolved by SDS-PAGE (4–20% gradient). Proteins were identified by silver staining. Molecular weight markers are indicated. Purified proteins are indicated by arrows.

FIG. 3 shows the results of analysis of ORFV2-VEGF protein using the VEGFR2 bioassay. Purified ORFV2-VEGF was tested for its ability to induce proliferation of Ba/F3 cells expressing a chimeric VEGFR-2. Bioassay cells were washed to remove IL-3 and then resuspended in dilutions of the ORFV2-VEGF, purified mouse $VEGF_{164}$ or medium alone for 48 hours at 37° C. in a humidified atmosphere of 10% $CO_2$. DNA synthesis was quantified by the addition of 1 $\mu$Ci of $^3$H-thymidine and counting the amount incorporated over a period of 4 hours. Values are expressed as mean ± standard deviations and are representative of 4 experiments.

FIG. 4 shows the VEGFR binding specificity of ORFV2-VEGF. Soluble fusion proteins consisting of the extracellular domain of VEGFRs and the Fc portion of human IgG1 were used to assess the receptor binding specificity of ORFV2-VEGF. Biosynthetically labeled conditioned medium derived from 293EBNA cells transfected with ORFV2-VEGF, mouse $VEGF_{164}$, human $VEGF_{165}$, human VEGF-DΔNΔC, human VEGF-CΔNΔC or vector alone were immunoprecipitated with protein A bound to (A) the VEGFR-1-Ig, VEGFR-2-Ig, VEGFR-3-Ig or (B) Neuropilin-1-Ig were eluted from washed beads with SDS-PAGE sample buffer and resolved by SDS-PAGE (4–20%). Only the ORFV2-VEGF and VEGF-DANAC were FLAG-tagged. Dried gels were visualized using phosphorimager analysis. The fusion protein used for each precipitation is listed above each panel.

FIG. 5 shows autophosphorylation of the VEGFRs receptor after stimulation by recombinant ORFV2-VEGF.

NIH3T3 cells expressing either VEGFR-2 or VEGFR-3 were made quiescent by starvation overnight in Dulbecco's Modified Eagle Medium(DMEM) containing 0.2% Bovine serum albumin. The cells were stimulated with either ORVF2-VEGF (100 ng/ml), VEGF$_{165}$ (50 ng/ml), human VEGF-CΔNΔC (100 ng/ml) or mock medium, lysed and immunoprecipitated using receptor-specific antibodies. The immunoprecipates were analyzed by phosphotyrosine immunoblotting. The apparent molecular weights of the tyrosyl phosphorylated VEGFR-2 and VEGFR-3 polypeptides are shown. An asterisk (*) marks a 200 kDa intracelluar form of VEGFR-2, which is not phosphorylated in response to receptor stimulation.

FIG. 6 shows the mitogenic effect of purified ORFV2-VEGF on human umbilical vein endothelial cells (HUVECs) HUVECs were exposed to purified ORFV2-VEGF, mouse VEGF$_{164}$ or human VEGF-DΔNΔC for 3 days. After 72 hours the amount of cellular proliferation was quantified by a 3-(4,5-dimethylthiazol-2-yl)-2,5-diphenyltetrazolium bromide (MTT, Sigma) assay measuring the conversion of a MTT substrate. The dotted line indicates the levels of stimulation achieved with medium alone. Values are expressed as a mean ± standard deviations and are representative of 3 experiments.

FIG. 7 shows the vascular permeability activity of purified ORFV2-VEGF in the Miles assay. Anesthetized guinea pigs were given intra-cardiac injections of Evans Blue dye. Purified ORFV2-VEGF, mouse VEGF$_{164}$ and appropriate controls were diluted in medium and 150 μl were injected intra-dermally into the shaved areas on the back of the animal. After 30 minutes, the animals were sacrificed and the skin excised (FIG. 7A) and then eluted in formamide and (FIG. 7B) the absorbance reading at 620 nm recorded. Values are expressed as mean ± standard deviations and are representative of 3 experiments.

FIG. 8 shows the nucleotide sequence encoding ORFV2-VEGF (SEQ ID NO:1).

FIG. 9 shows the amino acid sequence encoded by the nucleotide sequence of FIG. 8 (SEQ ID NO:2).

FIG. 10 shows the nucleotide sequence encoding ORFV10-VEGF (SEQ ID NO:10).

FIG. 11 shows the amino acid sequence (SEQ ID NO:11) encoded by the nucleotide sequence of FIG. 10.

DETAILED DESCRIPTION OF PREFERRED EMBODIMENTS

Figure 1A:
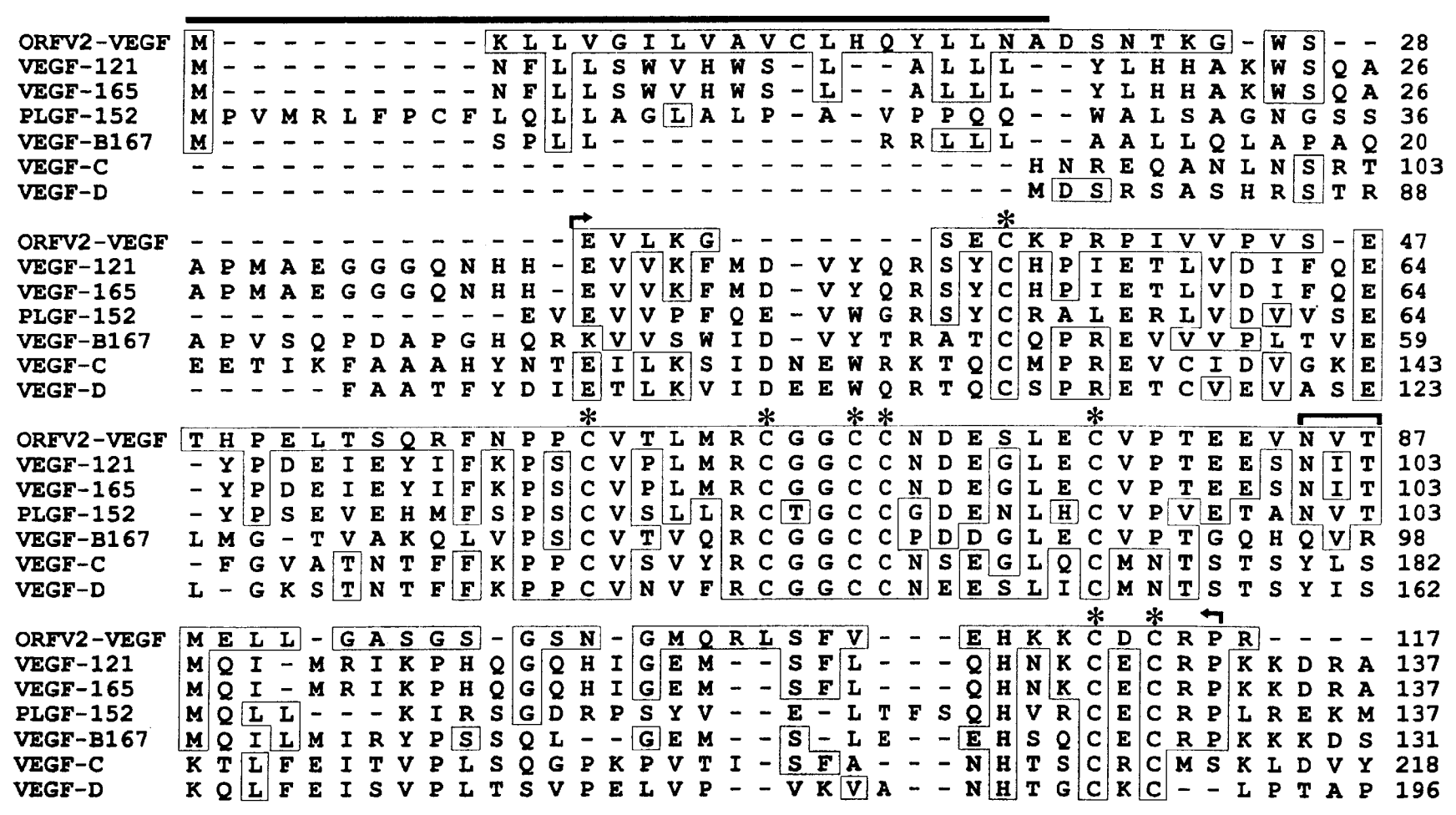
Figure 1B:
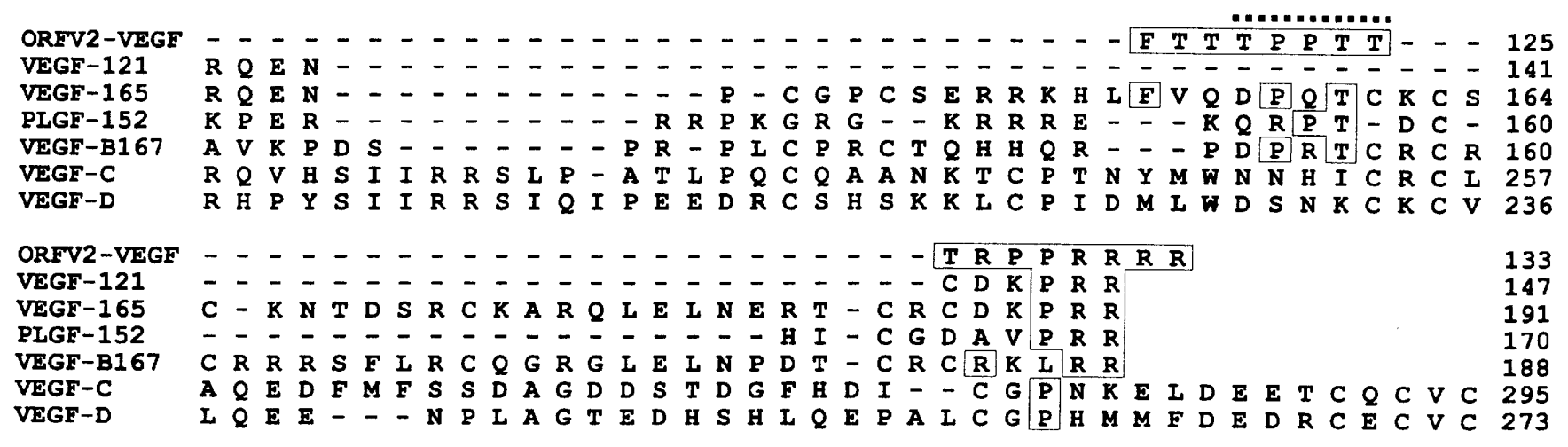
Figure 2A:
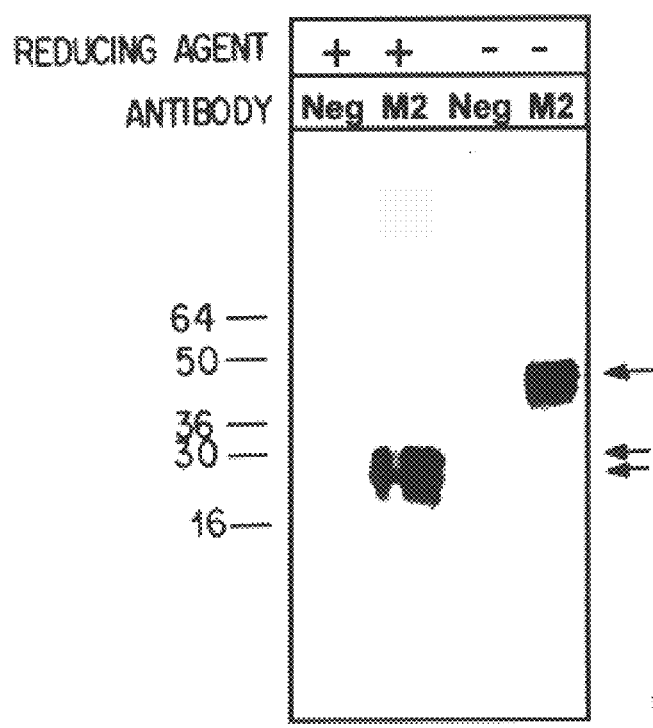

FIGS. 1A and 1B show a comparative sequence alignment of the amino acid sequences of ORFV2-VEGF with other members of the VEGF family of growth factors. The deduced amino acid sequence of ORFV2-VEGF was aligned with the sequences of VEGF$_{121}$ (SEQ ID NO:3), VEGF$_{165}$ (SEQ ID NO:4), PlGF (SEQ ID NO:5), VEGF-B$_{167}$ (SEQ ID NO:6), and truncated sequences of VEGF-C (SEQ ID NO:7) and VEGF-D (SEQ ID NO:8). Alignment of the predicted amino acid sequence of ORFV2-VEGF (SEQ ID NO:2) with members of the VEGF family demonstrates that ORFV2-VEGF has a high degree of sequence homology with the VEGF homology domain (VHD) of this family of proteins. ORFV2-VEGF contains all six cysteine residues of the cystine-knot motif which are absolutely conserved among family members. The conserved cysteine residues of the cystine knot motif are indicated with an asterisk (*). Several other invariant or highly conserved amino acids are indicated. ORFV2-VEGF does not contain the extended N- and C-terminal regions seen in VEGF-C and VEGF-D. Overall, ORFV2-VEGF is 43.3%, 34.3%, 25.4%, 26.9% and 33.6% identical to human VEGF$_{165}$ (SEQ ID NO:4), VEGF-B (SEQ ID NO:6), VEGF-C (SEQ ID NO:7), VEGF-D (SEQ ID NO:8) and PlGF (SEQ ID NO:5), respectively. The amino acid sequence of ORFV2-VEGF is 87% identical to NZ10. This sequence similarity of ORFV2-VEGF and NZ10 to the mammalian VEGFs raises the question of whether the structural relatedness extends to receptor binding and biological function.

The level of relatedness of ORFV2-VEGF/NZ10 to VEGF$_{165}$ suggests the possibility that ORFV2-VEGF/NZ10 is derived from the VEGF$_{165}$ gene but that sequence divergence may result in the changes which would affect receptor binding and hence biological function. However, it is also possible that ORFV2-VEGF/NZ10 is derived from another, yet unidentified, mammalian VEGF family member since another orf virus gene (a homolog of IL-10) shows 80% amino acid sequence identity to its mammalian counterpart. These predictions are complicated by the presence of a variant form of the viral VEGF in the NZ7 strain of the orf virus. Stain NZ7 encodes a protein which has only 23% amino acid identity with human VEGF, 43% identity with ORFV2-VEGF, and 40% identity with NZ10.

Example 1

Expression and Purification of ORFV2-VEGF and NZ10

A DNA fragment containing nucleotides 4 to 401 of the sequence shown in FIG. 8 (SEQ ID NO:1) of the VEGF-like gene of the orf virus strain NZ2, was prepared by polymerase chain reaction (PCR)using pVU89 as a template (Lyttle et al, J. Virol. 1994 68 84–92). This fragment was inserted into the pEFBOS-I-FLAG expression vector immediately upstream from the DNA sequence encoding the FLAG octapeptide. In addition, the cDNA encoding NZ10 (SEQ ID NO:10) was linked at its C-terminal with the sequence encoding the FLAG octapeptide. Protein synthesis gives rise to VEGF-like polypeptides that are tagged with the FLAG octapeptide at its C-terminus. These proteins were designated FLAG-tagged ORFV2-VEGF or FLAG-tagged NZ10. The FLAG-tagged NZ10 construct was subcloned into the pAPEX-3 expression vector and then transiently expressed in 293EBNA-1 cells using Fugene mediated transfection. After 24–72 hours the conditioned medium was collected and the FLAG-tagged proteins were purified using the M2-gel as described below. With respect to the vector including FLAG-tagged ORFV2-VEGF, it was transiently transfected into COS cells using the DEAE-Dextran method as described Aruffo and Seed, Proc. Natl. Acad. Sci. USA, 1987 84 8573–8577 and biosynthetically labeled with $^{35}$S -cysteine/methionine for 4 hours. After 3 days incubation, a portion of the transfected COS cells were metabolically labeled as described by Joukov et al, EMBO Journal 1996 15 290–298. The remaining culture was incubated for a total of 7 days. Conditioned cell culture was collected and clarified by centrifugation before the FLAG-tagged proteins were recovered by immunoprecipitation with either M2-gel (anti-FLAG) or control beads. The conditioned media was tested in the bioassay as described below, and the results demonstrated that the COS cells did in fact express and secrete biologically-active ORFV2-VEGF.

SDS-PAGE and Immunoblotting

Purified proteins or washed immunoprecipitates were combined with SDS-PAGE sample buffer under reducing (2% β-mercaptoethanol) or non-reducing conditions, boiled and resolved by SDS-PAGE. When required, proteins were transferred to nitrocellulose and blotted with M2 antibody. Under non-reducing conditions a band exhibiting a $M_r$ of approximately 44–48 kDa was observed, while under reducing conditions a faster migrating band exhibiting a $M_r$ of approximately 23–26 kDa was seen (see FIG. 2A). The bands detected are consistent with ORFV2-VEGF being a disulfide-linked homodimer with a monomeric $M_r$ of approximately 25 kDa. This is larger than the predicted size of 13,456 Da for ORFV2-VEGF and suggests modification by glycosylation. Examination of the ORFV2-VEGF sequence reveals one potential N-linked glycosylation site (Asn85–Thr87) and two potential O-linked glycosylation sites (Thr121–Thr125). N-glycanase treatment reduced the size of the ORFV2-VEGF monomer by about 5 kDa (not shown). The remaining size difference is believed due to O-linked glycosylation, the consensus sequences for which are present in the threonine/proline-rich C-terminus of ORFV2-VEGF. In FIG. 2A, the single arrow indicates the non-reduced form of ORFV2-VEGF and the double arrows the two species of reduced form.

Figure 2B:
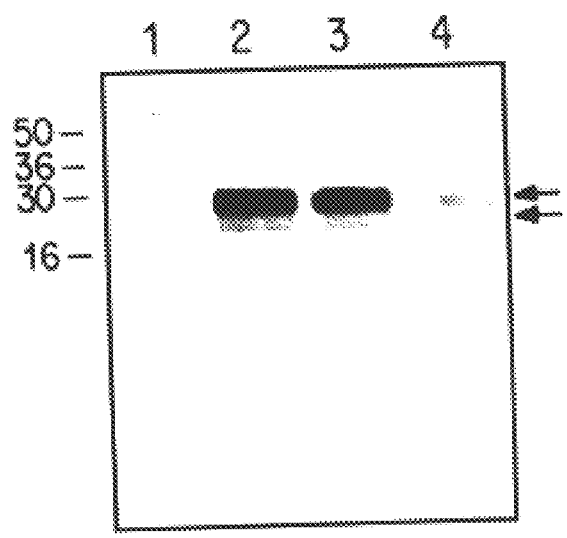

Unlabeled FLAG-tagged ORFV2-VEGF was enriched from the conditioned medium of transfected COS cells by affinity chromatography with M2 resin followed by elution with FLAG peptide. Analysis of this material by SDS-PAGE and silver staining (FIG. 2B) or Western blotting with anti-FLAG monoclonal antibodies (not shown) demonstrated species of the same $M_r$ as that seen following biosynthetic labeling. N-terminal sequencing of the secreted purified protein demonstrated a single sequence, and this was identical with the deduced amino acid sequence from residue 21 to 43 of FIG. 9 (SEQ ID NO:2) and confirmed the prediction that ORFV2-VEGF is a protein with a signal sequence of 20 amino acids.

For NZ10, the purified VEGF-like polypeptides also were found to be disulfide-linked homodimers (not shown). Under reducing conditions the monomers of NZ10 migrate at Mr approximately 30K (not shown).

Example 2

Bioassay for ORFV2-VEGF/NZ10 to Binding to VEGF Receptor-2

Figure 3:
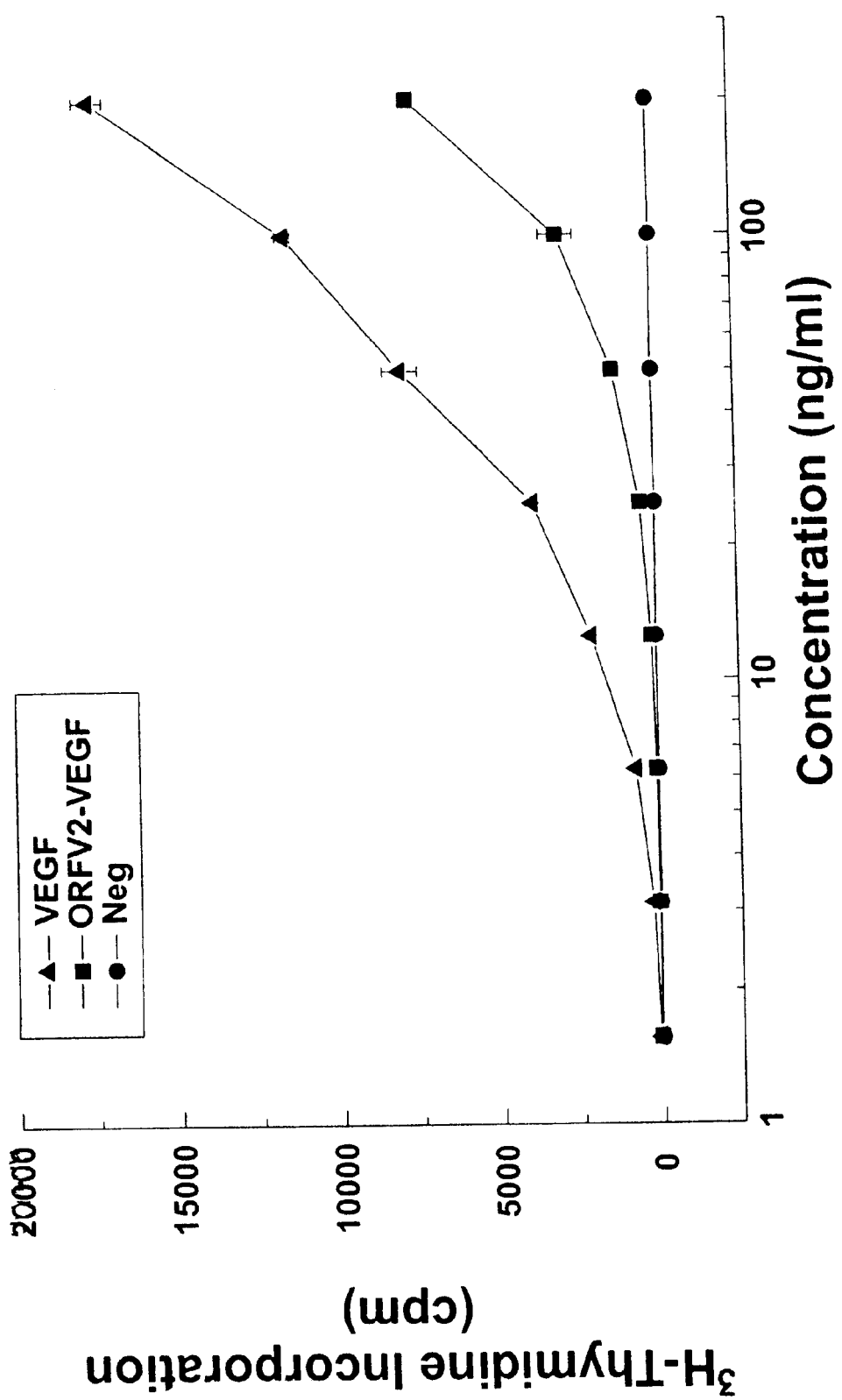

ORFV2-VEGF and NZ10 were tested in a bioassay which detects ligands for VEGFR-2. FIG. 3 shows the results of analysis of ORFV2-VEGF protein using the VEGFR2 bioassay. Results with NZ10 are not shown. The bioassay was performed using Ba/F3 cells which express a chimeric receptor consisting of the extracellular domain of mouse VEGFR-2 and the transmembrane and cytoplasmic domains of the mouse erythropoitin receptor (EpoR). The cells were maintained in Dulbecco's Modified Eagle Medium(DMEM) containing 10% fetal bovine serum (FBS), 50 mM L-glutamine, 50µg/ml gentamicin and 10% of the Walter and Eliza Hall Institute of Medical Research (WEHI) -3D-conditioned medium as a source of interleukin-3 (IL-3). Cells expressing the VEGFR-2-EpoR chimeric receptor were washed 3 times in phosphate buffered saline (PBS), and once in complete medium lacking IL-3. Cells ($10^4$) were aliquoted into 96-well microtiter plates containing dilutions of the test reagent or medium alone. Cells were incubated for 48 hours at 37° C. in a humidified atmosphere of 5% $CO_2$. Cell proliferation was quantified by the addition of 1 µCi of $^3$H-thymidine for 4 hours prior to harvesting. Incorporation of $^3$H-thymidine was determined using a cell harvester and β-counting.

Activation of the chimeric receptor rescues the cells from their dependence on IL-3 and causes the cells to proliferate in the absence of IL-3. VEGF, VEGF-CΔNΔC (the VEGF homology domain of VEGF-C) and VEGF-DΔNΔC (the VEGF homology domain of VEGF-D) which are all ligands for VEGFR-2, stimulate growth of this cell line in a specific and dose-dependent fashion (Achen et al, Proc. Natl. Acad. Sci. USA 1998 95 548–553). Purified ORFV2-VEGF was able to induce detectable DNA synthesis in the bioassay cell line at a concentration of 25 ng/ml. By comparison, VEGF was able to induce DNA synthesis in the bioassay cell line from a concentration of 5 ng/ml. Overall ORFV2-VEGF was about four-fold less potent in the bioassay compared to mouse VEGF. These results clearly demonstrate that ORFV2-VEGF can bind to and cross-link the extracellular domain of VEGFR-2 and induce a proliferation response. Similar results were found with NZ-2.

Example 3

ORFV2-VEGF Binding to Soluble VEGF Receptor-2 Extracellular Domains

To further assess the interactions between ORFV2-VEGF and the VEGFRs, ORFV2-VEGF was tested for its capacity to bind to soluble Ig-fusion proteins containing the extracellular domains of human VEGFR-1, VEGFR-2 and VEGFR-3. The fusion proteins, designated VEGFR-1-Ig, VEGFR-2-Ig and VEGFR-3-Ig, were transiently expressed in 293 EBNA cells. All Ig fusion proteins were human VEGFRs. Cells were incubated for 24 hours after transfection, washed with DMEM containing 0.2% bovine serum albumin and starved for 24 hours. The fusion proteins were then precipitated from the clarified conditioned medium using protein A-Sepharose beads. The beads were combined with 100 µl of 10x binding buffer (5% bovine serum albumin, 0.2% Tween 20 and 10 µg/ml heparin) and 900 µl of conditioned medium from 293 cells that had been transfected with expression plasmids encoding VEGF, VEGF-DΔNΔC,ORFV2-VEGF or control vector, then metabolically labeled with $^{35}$S-cysteine/methionine for 4 to 16 hours. After 2.5 hours, at room temperature, the Sepharose beads were washed 3 times with binding buffer at 4° C., once with phosphate buffered saline and boiled in SDS-PAGE buffer. Labeled proteins that were bound to the Ig-fusion proteins were analyzed by SDS-PAGE under reducing conditions. Radiolabeled proteins were detected using a phosphorimager analyzer.

Figure 4A:
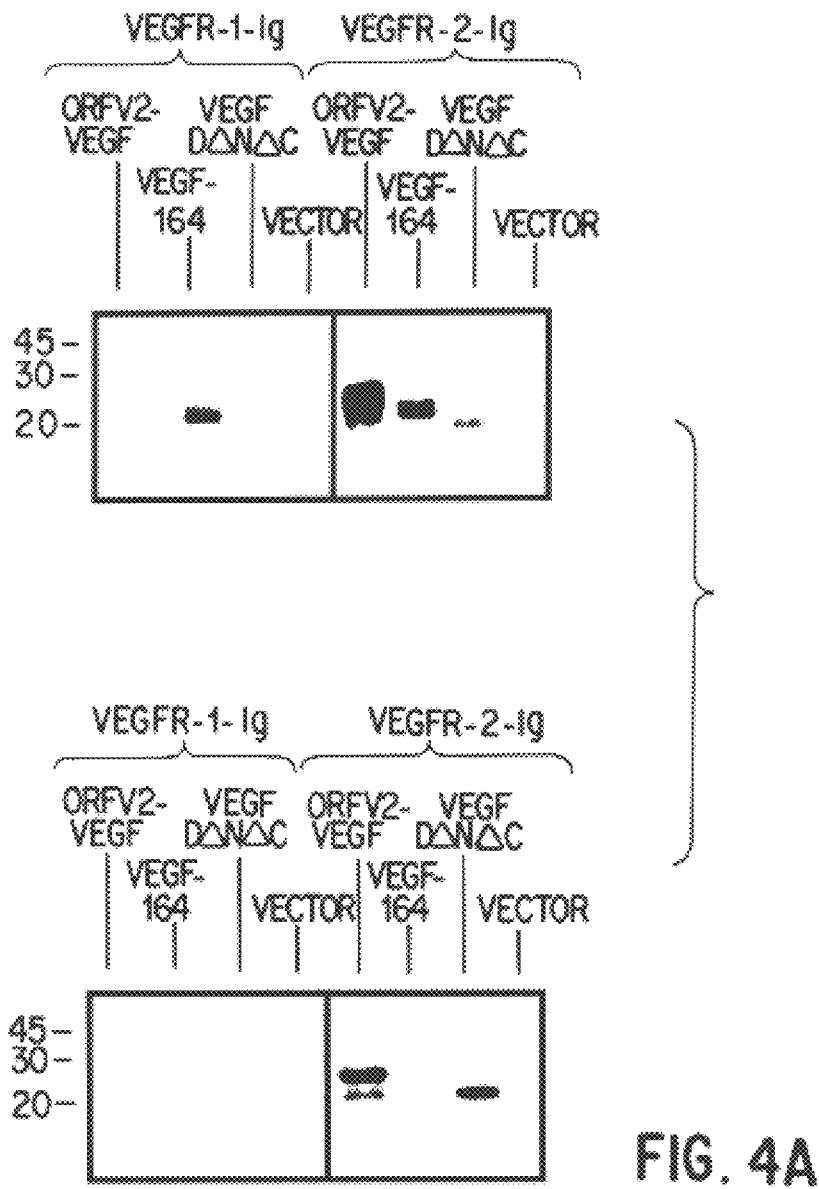
Figure 4B:
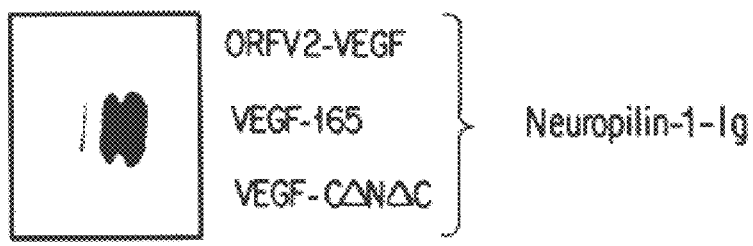

As seen in FIG. 4A, polypeptides corresponding to the size of ORFV2-VEGF were precipitated by VEGFR-2-Ig from the medium of cells expressing ORFV2-VEGF. In contrast, VEGFR-1-Ig or VEGFR-3-Ig precipitated no proteins from this medium. As expected a polypeptide of approximately 24 kDa was precipitated by VEGFR-1-Ig and VEGFR-2-Ig from the medium of cells expressing mouse $VEGF_{164}$ but was not precipitated by VEGFR-3-Ig. Also, as expected, a polypeptide of approximately 22 kDa was precipitated by VEGFR-2-Ig and VEGFR-3-Ig from the medium of cells expressing VEGF-DANAC but was not precipitated by VEGFR-1-Ig. No labeled polypeptides were precipitated by the three fusion proteins from the medium of cells transfected with the expression vector lacking sequences encoding VEGF's. ORFV2-VEGF was also tested for its ability to bind the neuropilin-1 receptor, a recently reported ligand for VEGF (FIG. 4B). The neuropilin-1-Ig fusion protein was able to precipitate $VEGF_{164}$ but not ORFV2-VEGF. In total these data indicate that the ORFV2-VEGF can bind to VEGFR-2 but not to VEGFR-1, VEGFR-3 or neuropilin-1. NZ10 was also found not to bind VEGFR-1. This receptor-binding specificity of ORFV2-VEGF and NZ10 is unique among the VEGF family of growth factors. Recent structural analyses of human VEGF identified residues thought to be important in binding to VEGFR-1 and VEGFR-2. In light of the receptor binding properties of ORFV2-VEGF, it is intriguing that the VEGF residues implicated as being critical in binding to VEGFR-1 are partially conserved in ORFV2-VEGF, while those involved in VEGFR-2 binding are not. Experiments which have determined the crystal structure of VEGF and predicted the residues critical for binding VEGFR-2 are Phe17, Ile46, Glu64, Gln79 and Ile83 and for binding VEGFR-1 are Asp63 and Glu64. The mechanism whereby ORFV2-VEGF binds to VEGFR-2 is clearly of interest; the lack of conservation of key residues suggests that the binding site for ORFV2-VEGF is different from that of VEGF.

Example 4

ORFV2-VEGF Activates VEGFR-2

Figure 5:
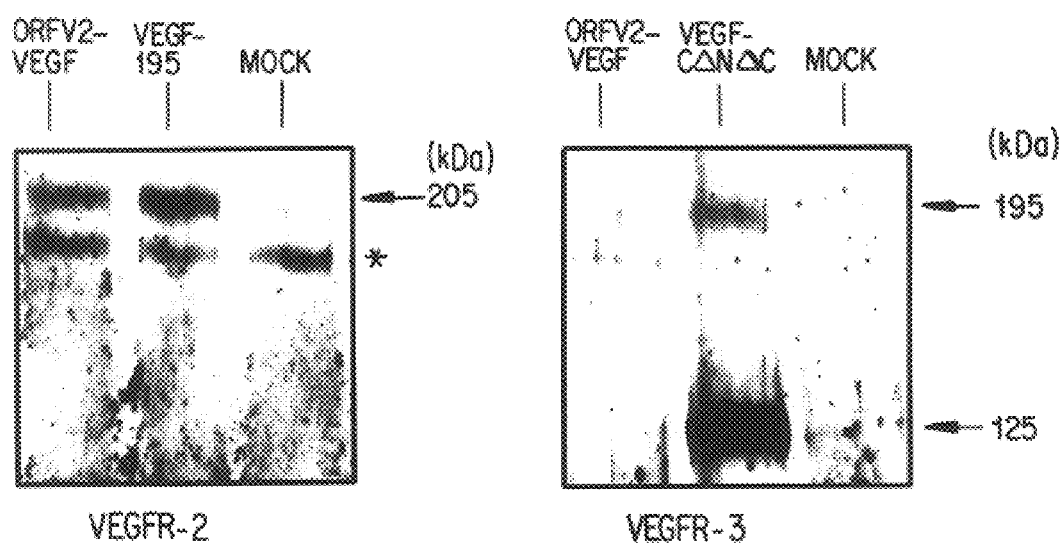

The ability of ORFV2-VEGF to induce tyrosine phosphorylation of human VEGFR-2 and human VEGFR-3 was examined. ORFV2-VEGF, VEGF$_{165}$ and VEGF-CΔNΔC were diluted in DMEM containing 0.2% bovine serum albumin and used to stimulate NIH3T3 cells expressing VEGFR-2 or VEGFR-3. After stimulation, cells were lysed and VEGFR-2 or VEGFR-3 were immunoprecipitated and analyzed by Western blot analysis with phosphotyrosine-specific monoclonal antibodies. As shown in FIG. 5, ORFV2-VEGF stimulated tyrosine kinase phosphorylation of VEGFR-2 but not VEGFR-3. As expected, the positive control proteins VEGF$_{165}$ and VEGF-CΔNΔC were able to induce phosphorylation of VEGFR-2 and VEGFR-3, respectively. These data demonstrate that ORFV2-VEGF can specifically induce phosphorylation of VEGFR-2.

Example 5

Mitogenicity of ORFV2-VEGF for Endothelial Cells

Figure 6:
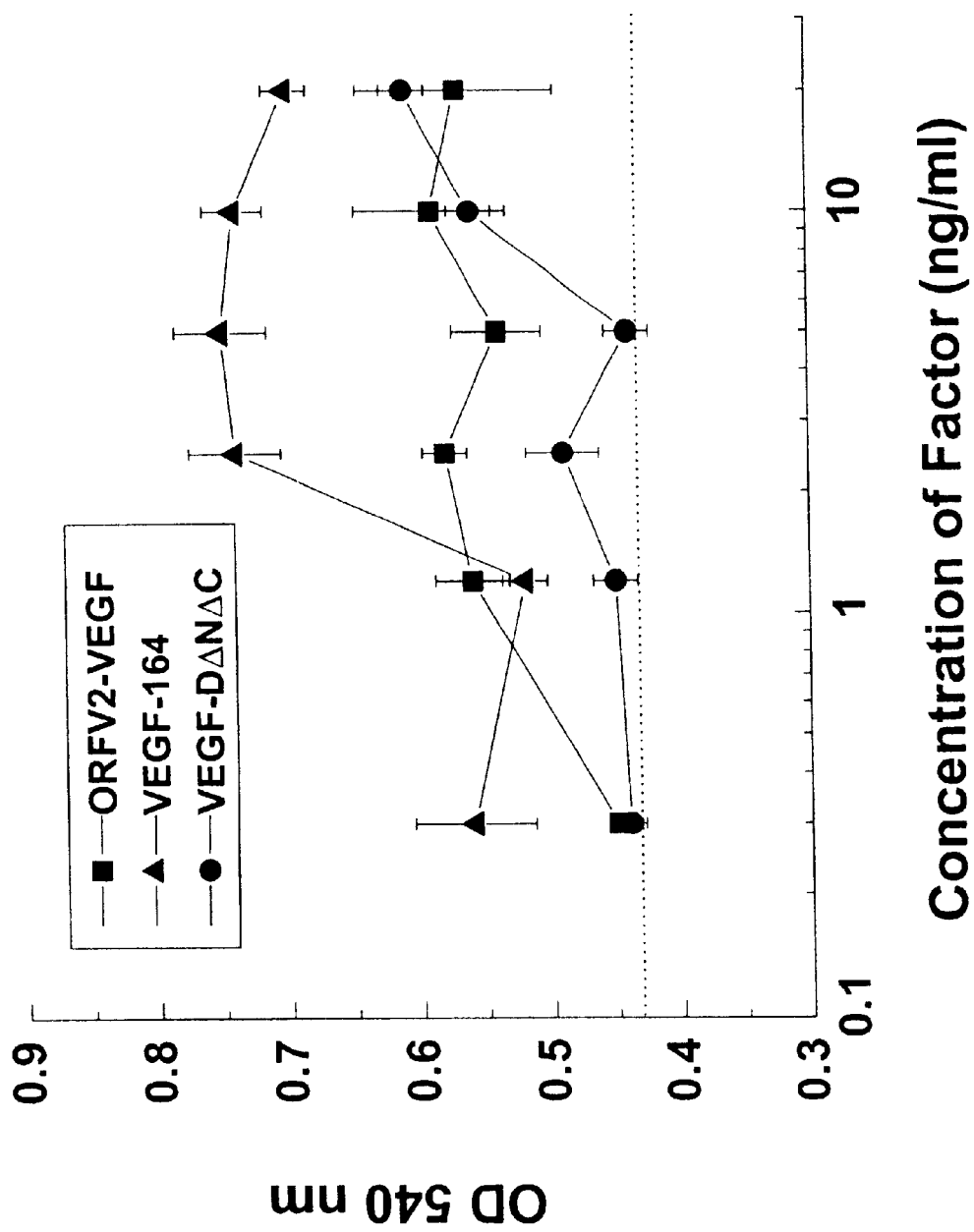

Members of the VEGF family of proteins show variable degrees of mitogenicity for endothelial cells. The mitogenic capacity of ORFV2-VEGF was tested using human umbilical vein endothelial cells (HUVECs). Cells grown in endothelial cell basal medium-2 (EBM-2, Clonetics) containing SingleQuots plus growth factor supplements and serum were removed with trypsin, washed and aliquoted at $10^3$ cells per well in a 96-well plate. Cells were allowed to adhere for 6 to 16 hours at 37° C. in EBM-2 medium plus serum without growth factors before samples of growth factor, diluted in the same medium was added. HUVECs were exposed to purified ORFV2-VEGF, mouse VEGF$_{164}$ or human VEGF-DΔNΔC for 3 days at 37° C. and then the cells were dissociated with trysin and counted. The amount of cellular proliferation was quantified by a 3-(4,5-dimethylthiazol-2-yl)-2,5-diphenyltetrazolium bromide (MTT) assay measuring the conversion of a MTT substrate. As seen in FIG. 6, ORFV2-VEGF (0.5–100 ng/ml) was able to stimulate an increase in the number of cells after 3 days compared to medium that did not contain added growth factor. Control proteins VEGF$_{164}$ and VEGF-CΔNΔC also stimulated the endothelial cells. The proliferative capacity of HUVECs exposed to ORFV2-VEGF was comparable to those grown with mouse VEGF164.

Example 6

Vascular Permeability Assay

Figure 7A:
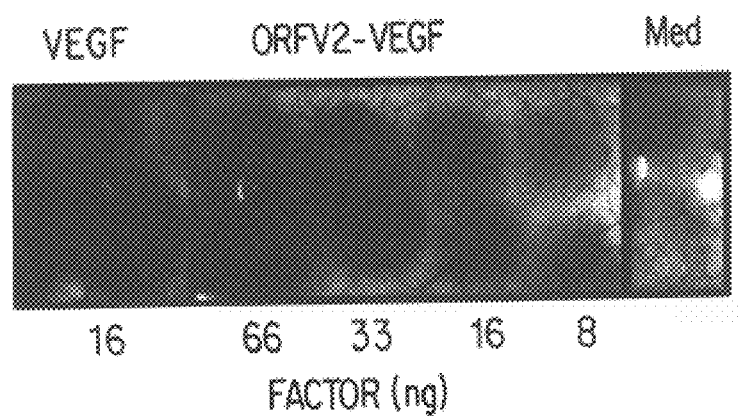
Figure 7B:
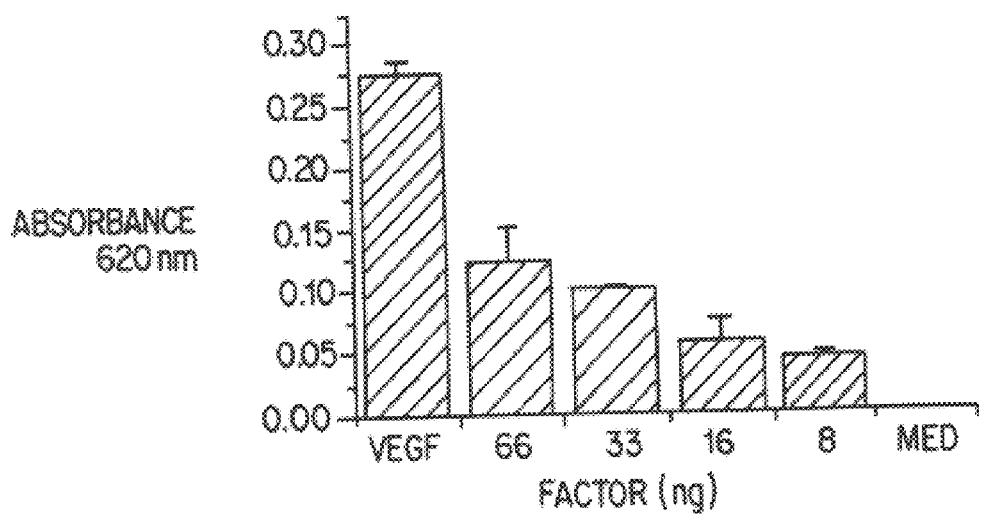

As orf virus lesions are characterized by swelling and fluid accumulation, the purified ORFV2-VEGF was tested for its ability to induce vascular permeability in a Miles Assay. Anesthetized guinea pigs were given intra-cardiac injections of 500 μl of 0.5% Evans Blue dye in phosphate buffered saline to introduce the dye into the bloodstream. Purified ORFV2-VEGF, mouse VEGF$_{164}$ and appropriate controls were diluted in medium and 150 μl were injected intra-dermally into the shaved areas on the back of the animal. After 30 minutes, the animals were sacrificed and the skin excised (FIG. 7A) and then eluted in formamide and (FIG. 7B) the absorbance reading at 620 nm recorded. The aliquots of ORFV2-VEGF contained 8 to 66 ng of factor. In comparison to medium alone there was detectable and dose-dependent permeability induced by the ORFV2-VEGF. ORFV2-VEGF is approximately five-fold less potent as a vascular permeability factor than mouse VEGF$_{164}$.

FIG. 8 shows the nucleotide sequence encoding ORFV2-VEGF (SEQ ID NO:1).

FIG. 9 shows the amino acid sequence encoded by the nucleotide sequence of FIG. 8 (SEQ ID NO:2).

The Examples above strongly suggest that ORFV2-VEGF is capable of inducing activation of the VEGFR-2 signaling pathway analogous to VEGF stimulation. ORFV2-VEGF is also capable of inducing the proliferation of endothelial cells. VEGFR-2 appears to be a major mediator of such activity. The ability of ORFV2-VEGF to induce vascular permeability, combined with its restricted receptor binding specificity, indicates that VEGFR-2 can mediate vascular permeability in the VEGFR family, as has been previously suggested by analysis of VEGF-C mutants. However, the presence of a novel receptor mediating permeability cannot be formally excluded.

BIOASSAYS TO DETERMINE THE FUNCTION OF ORFV2-VEGF

Other assays are conducted to evaluate whether ORFV2-VEGF or NZ10 has similar activities to VEGF, VEGF-C and/or VEGF-D in relation to endothelial cell function, angiogenesis and wound healing.

I. Assays of Endothelial Cell Function a) Endothelial Cell Proliferation

Endothelial cell growth assays are performed by methods well known in the art, eg. those of Ferrara & Henzel, Nature, 1989 380 439–443, Gospodarowicz et al Proc. Natl. Acad. Sci. USA, 1989 86 7311–7315, and/or Claffey et al, Biochim. Biophys. Acta, 1995 1246 1–9.

b) Cell Adhesion Assay

The effect of ORFV2-VEGF or NZ10 on adhesion of polmorphonuclear granulocytes to endothelial cells is tested.

c) Chemotaxis

The standard Boyden chamber chemotaxis assay is used to test the effect of ORFV2-VEGF or NZ10 on chemotaxis.

d) Plasminogen Activator Assay

Endothelial cells are tested for the effect of ORFV2-VEGF or NZ10 on plasminogen activator and plasminogen activator inhibitor production, using the method of Pepper et al, Biochem. Biophys. Res. Commun., 1991 181 902–906.

e) Endothelial Cell Migration Assay

The ability of ORFV2-VEGF or NZ10 to stimulate endothelial cells to migrate and form tubes is assayed as described in Montesano et al, Proc. Natl. Acad. Sci. USA, 1986 83 7297–7301. Alternatively, the three-dimensional collagen gel assay described by Joukov et al (1996) or a gelatinized membrane in a modified Boyden chamber (Glaser et al, Nature, 1980 288 483–484) may be used.

II Angiogenesis Assay

The ability of ORFV2-VEGF or NZ10 to induce an angiogenic response in chick chorioallantoic membrane is tested as described in Leung et al, Science, 1989 246 1306–1309. Alternatively the rat cornea assay of Rastinejad et al, Cell, 1989 56 345–355 may be used; this is an accepted method for assay of in vivo angiogenesis, and the results are readily transferrable to other in vivo systems.

III Wound Healing

The ability of ORFV2-VEGF or NZ10 to stimulate wound healing is tested in the most clinically relevant model available, as described in Schilling et al, Surgery, 1959 46 702–710 and utilized by Hunt et al, Surgery, 1967 114 302–307.

IV The Haemopoietic System

A variety of in vitro and in vivo assays using specific cell populations of the haemopoietic system are known in the art, and are outlined below. In particular a variety of in vitro murine stem cell assays using fluorescence-activated cell sorter purified cells are particularly convenient:

a) Repopulating Stem Cells

These are cells capable of repopulating the bone marrow of lethally irradiated mice, and have the $Lin^-$, $Rh^{h1}$, Ly-6A/$E^+$, c-$kit^+$ phenotype. ORFV2-VEGF or NZ10 is tested on these cells either alone, or by co-incubation with other factors, followed by measurement of cellular proliferation by $^3$H-thymidine incorporation.

b) Late Stage Stem Cells

These are cells that have comparatively little bone marrow repopulating ability, but can generate D13 CFU-S. These cells have the $Lin^-$, $Rh^{h1}$, Ly-6A/$E^+$, c-$kit^+$ phenotype. VEGF-D is incubated with these cells for a period of time, injected into lethally irradiated recipients, and the number of D13 spleen colonies enumerated.

c) Progenitor-Enriched Cells

These are cells that respond in vitro to single growth factors and have the $Lin^-$, $Rh^{h1}$, Ly-6A/$E^+$, c-$kit^+$ phenotype. This assay will show if ORFV2-VEGF or NZ10 can act directly on haemopoietic progenitor cells. ORFV2-VEGF or NZ10 is incubated with these cells in agar cultures, and the number of colonies present after 7–14 days is counted.

V Atherosclerosis

Smooth muscle cells play a crucial role in the development or initiation of atherosclerosis, requiring a change of their phenotype from a contractile to a senescent state. Macrophages, endothelial cells, T lymphocytes and platelets all play a role in the development of atherosclerotic plaques by influencing the growth and phenotypic modulations of smooth muscle cell. An in vitro assay using a modified Rose chamber in which different cell types are seeded on to opposite coverslips measures the proliferative rate and phenotypic modulations of smooth muscle cells in a multicellular environment, and is used to assess the effect of ORFV2-VEGF or NZ10 on smooth muscle cells.

VI Metastasis

The ability of ORFV2-VEGF or NZ10 to inhibit metastasis is assayed using the Lewis lung carcinoma model, for example using the method of Cao et al, J. Exp. Med., 1995 182 2069–2077.

VII ORFV2-VEGF or NZ10 in Other Cell Types

The effects of ORFV2-VEGF or NZ10 on proliferation, differentiation and function of other cell types, such as liver cells, cardiac muscle and other cells, endocrine cells and osteoblasts can readily be assayed by methods known in the art, such as $^3$H-thymidine uptake by in vitro cultures.

VIII Construction of ORFV2-VEGF or NZ10 Variants and Analogs

ORFV2-VEGF and NZ10 are members of the VEGF family of growth factors which exhibits a high degree of homology to the other members of the VEGF family. Both ORFV2-VEGF and NZ10 contain eight conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. ORFV2-VEGF and NZ10 will interact with protein tyrosine kinase growth factor receptors, and may also interact with other non-tyrosine kinase receptors.

In contrast to proteins where little or nothing is known about the protein structure and active sites needed for receptor binding and consequent activity, the design of active mutants of ORFV2-VEGF or NZ10 is greatly facilitated by the fact that a great deal is known about the active sites and important amino acids of the members of the PDGF family of growth factors.

Published articles elucidating the structure/activity relationships of members of the PDGF family of growth factors include for PDGF: Oestman et al, J. Biol. Chem., 1991 266 10073–10077; Andersson et al, J. Biol. Chem., 1992 267 11260–1266; Oefner et al, EMBO J., 1992 11 3921–3926; Flemming et al, Molecular and Cell Biol., 1993 13 4066–4076 and Andersson et al, Growth Factors, 1995 12 159–164; and for VEGF: Kim et al, Growth Factors, 1992 7 53–64; Pötgens et al, J. Biol. Chem., 1994 269 32879–32885 and Claffey et al, Biochem. Biophys. Acta, 1995 1246 1–9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located.

Based on this information, a person skilled in the biotechnology arts can design ORFV2-VEGF or NZ10 mutants with a very high probability of retaining ORFV2-VEGF or NZ10 activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure.

The formation of desired mutations at specifically targeted sites in a protein structure is considered to be a standard technique in the arsenal of the protein chemist (Kunkel et al, Methods in Enzymol., 1987 154 367–382). Examples of such site-directed mutagenesis with VEGF can be found in Potgens et al, J. Biol. Chem., 1994 269 32879–32885 and Claffey et al, Biochim. Biophys. Acta, 1995 1246 1–9. Indeed, site-directed mutagenesis is so common that kits are commercially available to facilitate such procedures (eg. Promega 1994–1995 Catalog., Pages 142–145).

The endothelial cell proliferating activity of ORFV2-VEGF or NZ10 mutants can be readily confirmed by well established screening procedures. For example, a procedure analogous to the endothelial cell mitotic assay described by Claffey et al, (Biochim. Biophys. Acta., 1995 1246 1–9) can be used. Similarly the effects of ORFV2-VEGF or NZ10 on proliferation of other cell types, on cellular differentiation and on human metastasis can be tested using methods which are well known in the art.

ORFV2-VEGF or NZ10 Contribution to Viral Lesions

It seems likely that the biological activities of ORFV2-VEGF or NZ10 contribute to the proliferative and highly vascular nature of orf viral lesions. This is supported by recent analysis of a recombinant orf virus in which the gene encoding ORFV2-VEGF has been deleted. Comparisons of lesions resulting from infection of sheep by wild type and recombinant ORFV2-VEGF-deficient orf virus indicate that in the absence of ORFV2-VEGF, skin lesions are significantly less vascularized.

The identification of a viral VEGF protein that is capable of subverting mammalian VEGF receptors to aid in its viral infection also raises the possibility that other viruses may act in a similar fashion.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof.

What is claimed is:

1. A method for activation of VEGF receptor 2, comprising the step of exposing cells bearing said receptor to an effective receptor activating dose of a polypeptide selected from the group consisting of ORFV2-VEGF and NZ10.

2. A method according to claim 1, wherein said method is carried out in vivo.

3. A method according to claim 1, wherein said method is carried out in vitro.

4. The method of claim 1, wherein the polypeptide is ORFV2-VEGF.

5. The method of claim 1, wherein the polypeptide is NZ10.

6. A method for specific activation of VEGF receptor 1: comprising the step of exposing cells bearing said receptor to an effective receptor activating dose of a polypeptide selected from the group consisting of ORFV2-VEGF and NZ10.

7. A method according to claim 6, wherein the VEGF receptor 1 is not activated.

8. The method of claim 6, wherein the polypeptide is ORFV2-VEGF.

9. The method of claim 6, wherein the polypeptide is NZ10.

10. A method for stimulating proliferation of endothelial or mesodermal cells, wherein the cells bear VEGF receptor 2, comprising activating the receptor via exposing said endothelial or mesodermal cells to an effective receptor-activating amount of a polypeptide selected from the group consisting of ORFV2-VEGF and NZ10, thereby stimulating the proliferation of the cells.

11. The method of claim 10 wherein the polypeptide is NZ10.

12. The method of claim 10, wherein the polypeptide is ORFV2-VEGF.

13. A method for modulating vascular permeability, comprising the step of administering an effective vascular permeability-modulating amount of an NZ10 polypeptide.

14. A method for stimulating proliferation of endothelial or mesodermal cells, comprising the step of exposing the endothelial or mesodermal cells to an effective endothelial or mesodermal cell proliferation-stimulating amount of a NZ10 polypeptide.

15. A method for modulating permeability of a vascular system in an animal in need thereof, wherein endothelial cells of the vascular system bear VEGF receptor 2, comprising activating the receptor via exposing said endothelial cells to an effective receptor-activating amount of a polypeptide selected from the group consisting of ORFV2-VEGF and NZ10, thereby modulating vascular permeability.

16. The method of claim 15, wherein the polypeptide is ORFV2-VEGF.

17. The method of claim 15, wherein the polypeptide is NZ10.

* * * * *

SEQUENCE LISTING

```
<160> NUMBER OF SEQ ID NOS: 11

<210> SEQ ID NO 1
<211> LENGTH: 402
<212> TYPE: DNA
<213> ORGANISM: Orf virus

<400> SEQUENCE: 1
atgaagttgc tcgtcggcat actagtagcc gtgtgcttgc accagtatct gctgaacgcg      60
gacagcaaca cgaaaggatg gtccgaagtg ctgaaaggca gcgagtgcaa gcctaggccg     120
attgttgttc ctgtaagcga gacgcaccca gagctgactt ctcagcggtt caacccgccg     180
tgtgtcacgt tgatgcgatg cggcgggtgc tgcaacgacg agagcttgga atgcgtcccc     240
acggaagaag taaacgtgac gatggaactc ctgggggcgt cgggctccgg tagtaacggg     300
atgcaacgtc tgagcttcgt agagcataag aaatgcgatt gtagaccacg attcacaacc     360
acgccaccga cgaccacaag gccgcccaga agacgccgct ag                        402

<210> SEQ ID NO 2
<211> LENGTH: 133
<212> TYPE: PRT
<213> ORGANISM: Orf virus

<400> SEQUENCE: 2

Met Lys Leu Leu Val Gly Ile Leu Val Ala Val Cys Leu His Gln Tyr
  1               5                  10                  15

Leu Leu Asn Ala Asp Ser Asn Thr Lys Gly Trp Ser Glu Val Leu Lys
             20                  25                  30

Gly Ser Glu Cys Lys Pro Arg Pro Ile Val Val Pro Val Ser Glu Thr
         35                  40                  45

His Pro Glu Leu Thr Ser Gln Arg Phe Asn Pro Pro Cys Val Thr Leu
     50                  55                  60

Met Arg Cys Gly Gly Cys Cys Asn Asp Glu Ser Leu Glu Cys Val Pro
 65                  70                  75                  80

Thr Glu Glu Val Asn Val Thr Met Glu Leu Leu Gly Ala Ser Gly Ser
                 85                  90                  95

Gly Ser Asn Gly Met Gln Arg Leu Ser Phe Val Glu His Lys Lys Cys
            100                 105                 110

Asp Cys Arg Pro Arg Phe Thr Thr Thr Pro Pro Thr Thr Thr Arg Pro
        115                 120                 125

Pro Arg Arg Arg Arg
    130
```

```
<210> SEQ ID NO 3
<211> LENGTH: 147
<212> TYPE: PRT
<213> ORGANISM: Homo sapiens

<400> SEQUENCE: 3

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
 65                  70                  75                  80

Met Arg Cys Gly Gly Cys Ser Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Cys Asp Lys
    130                 135                 140

Pro Arg Arg
145

<210> SEQ ID NO 4
<211> LENGTH: 191
<212> TYPE: PRT
<213> ORGANISM: Homo sapiens

<400> SEQUENCE: 4

Met Asn Phe Leu Leu Ser Trp Val His Trp Ser Leu Ala Leu Leu Leu
 1               5                  10                  15

Tyr Leu His His Ala Lys Trp Ser Gln Ala Ala Pro Met Ala Glu Gly
                20                  25                  30

Gly Gly Gln Asn His His Glu Val Val Lys Phe Met Asp Val Tyr Gln
            35                  40                  45

Arg Ser Tyr Cys His Pro Ile Glu Thr Leu Val Asp Ile Phe Gln Glu
        50                  55                  60

Tyr Pro Asp Glu Ile Glu Tyr Ile Phe Lys Pro Ser Cys Val Pro Leu
 65                  70                  75                  80

Met Arg Cys Gly Gly Cys Ser Asn Asp Glu Gly Leu Glu Cys Val Pro
                85                  90                  95

Thr Glu Glu Ser Asn Ile Thr Met Gln Ile Met Arg Ile Lys Pro His
            100                 105                 110

Gln Gly Gln His Ile Gly Glu Met Ser Phe Leu Gln His Asn Lys Cys
        115                 120                 125

Glu Cys Arg Pro Lys Lys Asp Arg Ala Arg Gln Glu Asn Pro Cys Gly
    130                 135                 140

Pro Cys Ser Glu Arg Arg Lys His Leu Phe Val Gln Asp Pro Gln Thr
145                 150                 155                 160

Cys Lys Cys Ser Cys Lys Asn Thr His Ser Arg Cys Lys Ala Arg Gln
                165                 170                 175
```

```
Leu Glu Leu Asn Glu Arg Thr Cys Arg Cys Asp Lys Pro Arg Arg
            180                 185                 190
```

<210> SEQ ID NO 5
<211> LENGTH: 170
<212> TYPE: PRT
<213> ORGANISM: Homo sapiens

<400> SEQUENCE: 5

```
Met Pro Val Met Arg Leu Phe Pro Cys Phe Leu Gln Leu Leu Ala Gly
  1               5                  10                  15

Leu Ala Leu Pro Ala Val Pro Gln Gln Trp Ala Leu Ser Ala Gly
                 20                  25                  30

Asn Gly Ser Ser Glu Val Glu Val Pro Phe Gln Glu Val Trp Gly
             35                  40                  45

Arg Ser Tyr Cys Arg Ala Leu Glu Arg Leu Val Asp Val Val Ser Glu
         50                  55                  60

Tyr Pro Ser Glu Val Glu His Met Phe Ser Pro Ser Cys Val Ser Leu
 65                  70                  75                  80

Leu Arg Cys Thr Gly Cys Cys Gly Asp Glu Asp Leu His Cys Val Pro
                 85                  90                  95

Val Glu Thr Ala Asn Val Thr Met Gln Leu Leu Lys Ile Arg Ser Gly
                100                 105                 110

Asp Arg Pro Ser Tyr Val Glu Leu Thr Phe Ser Gln His Val Arg Cys
            115                 120                 125

Glu Cys Arg Pro Leu Arg Glu Lys Met Lys Pro Glu Arg Arg Arg Pro
130                 135                 140

Lys Gly Arg Gly Lys Arg Arg Glu Asn Gln Arg Pro Thr Asp Cys
145                 150                 155                 160

His Leu Cys Gly Asp Ala Val Pro Arg Arg
                165                 170
```

<210> SEQ ID NO 6
<211> LENGTH: 188
<212> TYPE: PRT
<213> ORGANISM: Homo sapiens

<400> SEQUENCE: 6

```
Met Ser Pro Leu Leu Arg Arg Leu Leu Leu Ala Ala Leu Leu Gln Leu
  1               5                  10                  15

Ala Pro Ala Gln Ala Pro Val Ser Gln Pro Asp Ala Pro Gly His Gln
                 20                  25                  30

Arg Lys Val Val Ser Trp Ile Asp Val Tyr Thr Arg Ala Thr Cys Gln
             35                  40                  45

Pro Arg Glu Val Val Val Pro Leu Thr Val Glu Leu Met Gly Thr Val
 50                  55                  60

Ala Lys Gln Leu Val Pro Ser Cys Val Thr Val Gln Arg Cys Gly Gly
 65                  70                  75                  80

Cys Cys Pro Asp Asp Gly Leu Glu Cys Val Pro Thr Gly Gln His Gln
                 85                  90                  95

Val Arg Met Gln Ile Leu Met Ile Arg Tyr Pro Ser Ser Gln Leu Gly
                100                 105                 110

Glu Met Ser Leu Glu Glu His Ser Gln Cys Glu Cys Arg Pro Lys Lys
            115                 120                 125

Lys Asp Ser Ala Val Lys Pro Asp Ser Pro Arg Pro Leu Cys Pro Arg
130                 135                 140
```

```
Cys Thr Gln His His Gln Arg Pro Asp Pro Arg Thr Cys Arg Cys Arg
145                 150                 155                 160

Cys Arg Arg Arg Ser Phe Leu Arg Cys Gln Gly Arg Gly Leu Glu Leu
            165                 170                 175

Asn Pro Asp Thr Cys Arg Cys Arg Lys Leu Arg Arg
        180                 185

<210> SEQ ID NO 7
<211> LENGTH: 228
<212> TYPE: PRT
<213> ORGANISM: Homo sapiens

<400> SEQUENCE: 7

His Asn Arg Glu Gln Ala Asn Leu Asn Ser Arg Thr Glu Glu Thr Ile
1               5                   10                  15

Lys Phe Ala Ala Ala His Tyr Asn Thr Glu Ile Leu Lys Ser Ile Asp
            20                  25                  30

Asn Glu Trp Arg Lys Thr Gln Cys Met Pro Arg Glu Val Cys Ile Asp
        35                  40                  45

Val Gly Lys Glu Phe Gly Val Ala Thr Asn Thr Phe Phe Lys Pro Pro
    50                  55                  60

Cys Val Ser Val Tyr Arg Cys Gly Gly Cys Cys Asn Ser Glu Gly Leu
65                  70                  75                  80

Gln Cys Met Asn Thr Ser Thr Ser Tyr Leu Ser Lys Thr Leu Phe Glu
                85                  90                  95

Ile Thr Val Pro Leu Ser Gln Gly Pro Lys Pro Val Thr Ile Ser Phe
            100                 105                 110

Ala Asn His Thr Ser Cys Arg Cys Met Ser Lys Leu Asp Val Tyr Arg
        115                 120                 125

Gln Val His Ser Ile Ile Arg Arg Ser Leu Pro Ala Thr Leu Pro Gln
    130                 135                 140

Cys Gln Ala Ala Asn Lys Thr Cys Pro Thr Asn Tyr Met Trp Asn Asn
145                 150                 155                 160

His Ile Cys Arg Cys Leu Ala Gln Glu Asp Phe Met Phe Ser Ser Asp
                165                 170                 175

Ala Gly Asp Asp Ser Thr Asp Gly Phe His Asp Ile Cys Gly Pro Asn
            180                 185                 190

Lys Glu Leu Asp Glu Glu Thr Cys Gln Cys Val Cys Arg Ala Gly Leu
        195                 200                 205

Arg Pro Ala Ser Cys Gly Pro His Lys Glu Leu Asp Arg Asn Ser Cys
    210                 215                 220

Gln Cys Val Cys
225

<210> SEQ ID NO 8
<211> LENGTH: 197
<212> TYPE: PRT
<213> ORGANISM: Homo sapiens

<400> SEQUENCE: 8

Met Asp Ser Arg Ser Ala Ser His Arg Ser Thr Arg Phe Ala Ala Thr
1               5                   10                  15

Phe Tyr Asp Ile Glu Thr Leu Lys Val Ile Asp Glu Glu Trp Gln Arg
            20                  25                  30

Thr Gln Cys Ser Pro Arg Glu Thr Cys Val Glu Val Ala Ser Glu Leu
        35                  40                  45
```

```
Gly Lys Ser Thr Asn Thr Phe Phe Lys Pro Pro Cys Val Asn Val Phe
     50                  55                  60
Arg Cys Gly Gly Cys Cys Asn Glu Glu Ser Leu Ile Cys Met Asn Thr
 65                  70                  75                  80
Ser Thr Ser Tyr Ile Ser Lys Gln Leu Phe Glu Ile Ser Val Pro Leu
                 85                  90                  95
Thr Ser Val Pro Glu Leu Val Pro Val Lys Val Ala Asn His Thr Gly
                100                 105                 110
Cys Lys Cys Leu Pro Thr Ala Pro Arg His Pro Tyr Ser Ile Ile Arg
            115                 120                 125
Arg Ser Ile Gln Ile Pro Glu Glu Asp Arg Cys Ser His Ser Lys Lys
130                 135                 140
Leu Cys Pro Ile Asp Met Leu Trp Asp Ser Asn Lys Cys Lys Cys Val
145                 150                 155                 160
Leu Gln Glu Glu Asn Pro Leu Ala Gly Thr Glu Asp His Ser His Leu
                165                 170                 175
Gln Glu Pro Ala Leu Cys Gly Pro His Met Met Phe Asp Glu Asp Arg
            180                 185                 190
Cys Glu Cys Val Cys
            195
```

<210> SEQ ID NO 9
<211> LENGTH: 13
<212> TYPE: PRT
<213> ORGANISM: Orf virus
<220> FEATURE:
<221> NAME/KEY: UNSURE
<222> LOCATION: (2)
<223> OTHER INFORMATION: Any amino acid
<220> FEATURE:
<221> NAME/KEY: UNSURE
<222> LOCATION: (4)..(7)
<223> OTHER INFORMATION: Any amino acid
<220> FEATURE:
<221> NAME/KEY: UNSURE
<222> LOCATION: (10)
<223> OTHER INFORMATION: Any amino acid
<220> FEATURE:
<223> OTHER INFORMATION: This amino acid sequence motif can be found at
      residue positions 59-71 of SEQ ID NO:2

<400> SEQUENCE: 9

```
Pro Xaa Cys Xaa Xaa Xaa Xaa Arg Cys Xaa Gly Cys Cys
 1               5                  10
```

<210> SEQ ID NO 10
<211> LENGTH: 399
<212> TYPE: DNA
<213> ORGANISM: Orf virus

<400> SEQUENCE: 10

```
atgaagttgc tcgtcggcat actggtagcc gtgtgcttgc accagtatct gctgaacgcg      60
gacagcacga aaacatggtc cgaggtgttt gaaagcagta gtgcaagcc aaggccaacg     120
gtcgttcccg taggcgaggc gcacccagag ctaacttctc agcggttcaa cccgcagtgt    180
gtcacagtga tgcgatgcgg cggtgctgc aacgacgaga gcttggaatg cgtccccacg     240
gaagaggcaa acgtgacgat gcaactcatg ggggcgtcgg tctccggtgg taacgggatg    300
caacatttga tattcgtaga gcataagaaa tgcgattgta aaccacgact cacaaccacg    360
ccaccgacga ccacaaggcc gcccagaaga cgccgctag                           399
```

-continued

```
<210> SEQ ID NO 11
<211> LENGTH: 132
<212> TYPE: PRT
<213> ORGANISM: Orf virus

<400> SEQUENCE: 11

Met Lys Leu Leu Val Gly Ile Leu Val Ala Val Cys Leu His Gln Tyr
 1               5                  10                  15

Leu Leu Asn Ala Asp Ser Thr Lys Thr Trp Ser Glu Val Phe Glu Ser
            20                  25                  30

Ser Lys Cys Lys Pro Arg Pro Thr Val Val Pro Val Gly Glu Ala His
        35                  40                  45

Pro Glu Leu Thr Ser Gln Arg Phe Asn Pro Gln Cys Val Thr Val Met
    50                  55                  60

Arg Cys Gly Gly Cys Cys Asn Asp Glu Ser Leu Glu Cys Val Pro Thr
65                  70                  75                  80

Glu Glu Ala Asn Val Thr Met Gln Leu Met Gly Ala Ser Val Ser Gly
                85                  90                  95

Gly Asn Gly Met Gln His Leu Ile Phe Val Glu His Lys Lys Cys Asp
            100                 105                 110

Cys Lys Pro Arg Leu Thr Thr Thr Pro Pro Thr Thr Thr Arg Pro Pro
        115                 120                 125

Arg Arg Arg Arg
    130
```